(12) United States Patent
Glombik et al.

(10) Patent No.: US 6,498,156 B2
(45) Date of Patent: Dec. 24, 2002

(54) DIPHENYLAZETIDINONE DERIVATIVES, PROCESS FOR THEIR PREPARATION, MEDICAMENTS COMPRISING THESE COMPOUNDS AND THEIR USE

(75) Inventors: Heiner Glombik, Hofheim (DE); Werner Kramer, Mainz-Laubenheim (DE); Stefanie Flohr, Eppstein (DE); Wendelin Frick, Hünstetten-Beuerbach (DE); Hubert Heuer, Schwabenheim (DE); Gerhard Jaehne, Frankfurt am Main (DE); Andreas Lindenschmidt, Bad Soden (DE); Hans-Ludwig Schaefer, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/021,028

(22) Filed: Dec. 19, 2001

(65) Prior Publication Data

US 2002/0128252 A1 Sep. 12, 2002

(30) Foreign Application Priority Data

Dec. 21, 2000 (DE) .......................................... 100 64 402
Nov. 7, 2001 (DE) .......................................... 101 54 520

(51) Int. Cl.⁷ .................... A61K 31/397; C07D 409/12; A61P 9/00
(52) U.S. Cl. .................... 514/210.02; 540/200
(58) Field of Search .................... 540/200; 514/210.02

(56) References Cited

U.S. PATENT DOCUMENTS 5,756,470 A  5/1998  Yumibe et al.

FOREIGN PATENT DOCUMENTS

| WO | WO95/08532 | 3/1995 |
| WO | WO95/35277 | 12/1995 |
| WO | WO96/08484 | 3/1996 |
| WO | WO96/19450 | 6/1996 |
| WO | WO00/01687 | 1/2000 |

OTHER PUBLICATIONS

"Ezetimibe—Hypolipidemic Cholesterol Absorption Inhibitor", Drugs of the Future, 25(7), pp. 679–685, (2000).
Hilgers et al., "Caco–2 Cell Monolayers as a Model for Drug Transport Across the Intestinal Mucosa", Pharmaceutical Research, 7(9), pp. 902–910, (1990).

Primary Examiner—Joseph K. McKane
Assistant Examiner—Andrea D. Small
(74) Attorney, Agent, or Firm—Finnegan, Henderson, Farabow, Garrett & Dunner, LLP

(57) ABSTRACT

Compounds of the formula I,

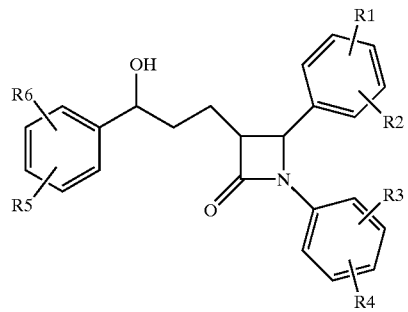

in which R1, R2, R3, R4, R5, and R6 have the meanings given in the description, and their physiologically acceptable salts. The compounds are suitable for use, for example, as hypolipidemics.

14 Claims, No Drawings

DIPHENYLAZETIDINONE DERIVATIVES, PROCESS FOR THEIR PREPARATION, MEDICAMENTS COMPRISING THESE COMPOUNDS AND THEIR USE

This application claims the benefit of priority under 35 U.S.C. §119(a) to German patent application no. 10064402.3, filed on Dec. 21, 2000, and German patent application no. 10154520.7, filed on Nov. 7, 2001. The contents of both priority documents are incorporated by reference herein.

The invention relates to substituted diphenylazetidinones, to their physiologically acceptable salts and to derivatives having physiological function.

Diphenylazetidinones (such as, for example, ezetimibe) and their use for treating hyperlipidemia and arteriosclerosis and hypercholesterolemia have already been described [cf. Drugs of the Future 2000, 25(7):679–685)].

It was an object of the invention to provide further compounds having a therapeutically utilizable hypolipidemic action. In particular, it was an object to find novel compounds which, compared to the compounds described in the prior art, are absorbed to a very low extent. Very low absorption is to be understood as meaning an intestinal absorption of less than 10%, preferably less than or equal to 5%. In particular, absorption of the novel compounds should be less than that of ezetimibe. Pharmaceutically active compounds which are absorbed to a very low extent generally have considerably fewer side-effects.

Accordingly, an embodiment of the invention relates to compounds of the formula I,

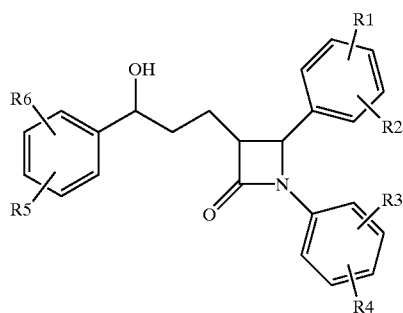

in which

R1, R2, R3, R4, R5, R6 independently of one another are
($C_0$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)- or —NH—; or H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one or more hydrogens in the alkylene radicals may be replaced by fluorine; or $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl or $SO_2$—($H_2$)$_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N(($C_1$–$C_6$)-alkyl)$_2$, NH($C_1$–$C_7$)-acyl, phenyl or O—($CH_2$)$_n$-phenyl, where n=0–6, where the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$;

L is shown connected to ($C_0$–$C_{30}$)-alkylene as follows:

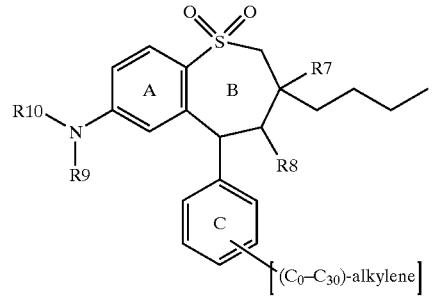

R7 is methyl, ethyl, propyl or butyl;
R8 is H, OH, $NH_2$ or NH—($C_1$–$C_6$)-alkyl;
R9 is methyl, ethyl, propyl or butyl;
R10 is methyl, ethyl, propyl or butyl;

wherein at least one of the radicals R1 to R6 has the meaning
($C_0$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)- or —NH—, and its pharmaceutically acceptable salts.

Another embodiment of the invention relates to compounds of the formula I, in which at least one of the radicals R1 to R6 has the meaning ($C_0$–$C_{30}$)-alkylene-L, where one or more carbon atoms of the alkylene radical may be replaced by —O—, —(C=O)— or —NH—.

Another embodiment of the invention relates to compounds of the formula I, in which one of the radicals R1 or R3 has the meaning —($C_0$–$C_{30}$)-alkylene-L, where one or more carbon atoms of the alkylene radical may be replaced by —O—, —(C=O)— or —NH—.

Another embodiment of the invention relates to compounds of the formula I, in which one of the radicals R1 or R3 has the meaning —($CH_2$)$_{0-1}$—NH—(C=O)$_{0-1}$—($C_3$–$C_{25}$)-alkylene-(C=O)$_{0-1}$—NH—L, where one or more carbon atoms of the alkylene radical may be replaced by oxygen atoms.

One of the radicals R1 to R6 may be, for example, attached to the L radical in the meta position of ring C of the L group.

Owing to their increased solubility in water, compared to the parent compounds, pharmaceutically acceptable salts are particularly suitable for medical applications. These salts should have a pharmaceutically acceptable anion or cation. Suitably pharmaceutically acceptable acid addition salts of the compounds according to the invention are salts of inorganic acids, such as hydrochloric acid, hydrobromic acid, phosphoric acid, metaphosphoric acid, nitric acid, sulfonic acid and sulfuric acid, and of organic acids, such as acetic acid, benzenesulfonic acid, benzoic acid, citric acid, ethanesulfonic acid, fumaric acid, gluconic acid, glycolic acid, isothionic acid, lactic acid, lactobionic acid, maleic acid, malic acid, methanesulfonic acid, succinic acid, p-toluenesulfonic acid, tartaric acid and trifluoroacetic acid, for example. For medical purposes, very particular preference is given to using the chloride salt. Suitable pharmaceutically acceptable basic salts are ammonium salts, alkali metal salts (such as sodium and potassium salts) and alkaline earth metal salts (such as magnesium and calcium salts).

The scope of the invention also includes salts having a pharmaceutically unacceptable anion, which salts may be useful intermediates for preparing or purifying pharmaceutically acceptable salts and/or for use in nontherapeutic, for example in vitro, applications.

Here, the term "derivative having physiological function" refers to any physiologically acceptable derivative of a compound according to the invention, for example an ester, capable of forming, upon administration to a mammal, for example man, such a compound or an active metabolite (directly or indirectly).

A further aspect of this invention are prodrugs of the compounds according to the invention. Such prodrugs can be metabolized in vivo to give a compound according to the invention. These prodrugs may or may not be active in their own right.

The compounds according to the invention can also be present in various polymorphic forms, for example as amorphous and crystalline polymorphous forms. The scope of the invention includes all polymorphic forms of the compounds according to the invention, which form a further aspect of the invention. The compounds of the invention may also exist in the form of solvates.

The compounds of the formula I and their pharmaceutically acceptable salts, esters, prodrugs and derivatives having physiological function are ideal medicaments for treating an impaired lipid metabolism, in particular hyperlipidemia. The compounds of the formula I are also suitable for modulating the serum cholesterol concentration and for treating arteriosclerotic symptoms. The compounds of the invention are also suitable for the treatment of insulin resistance.

As used here, "treatment" or "therapy" of a condition and "treating" a condition can mean successfully eliminating the condition, reducing the effects associated with it, and/or reducing its severity. It also includes administering the relevant compounds to a patient to avoid recurrence of a condition. It also includes avoiding the onset of a condition by administering the relevant compounds to patients falling into a risk group or category for developing the particular condition. Those skilled in the art can routinely identify patients likely to present with a given condition, thereby qualifying as candidates for treatment.

The compound(s) of the formula (I) can also be administered in combination with other active compounds.

The amount of a compound of the formula (I) required to achieve the desired biological effect depends on a number of factors, for example on the specific compound chosen, on the intended use, on the mode of administration and on the clinical condition of the patient. In general, the daily dose is in the range from 0.1 mg to 100 mg (typically from 0.1 mg to 50 mg) per day per kilogram of bodyweight, for example 0.1–10 mg/kg/day. Tablets or capsules may contain, for example, from 0.01 to 100 mg, typically from 0.02 to 50 mg. In the case of pharmaceutically acceptable salts, the abovementioned weight data relate to the weight of the diphenylazetidinone-ion derived from the salt. For the therapy of the abovementioned conditions, the compounds of the formula (I) can be used themselves as the compound, but preferably they are present in the form of a pharmaceutical composition with an acceptable carrier. The carrier must of course be acceptable in the sense that it is compatible with the other constituents of the composition and is not harmful to the health of the patient. The carrier can be a solid or a liquid or both and is preferably formulated with the compound as an individual dose, for example as a tablet, which can contain from 0.05% to 95% by weight of the active compound. Further pharmaceutically active substances can also be present, including further compounds of the formula (I). The pharmaceutical compositions according to the invention can be prepared by one of the known pharmaceutical methods, which essentially consists in mixing the constituents with pharmaceutically acceptable carriers and/or auxiliaries.

Pharmaceutical compositions according to the invention are those which are suitable for oral or peroral (e.g. sublingual) administration, although the most suitable manner of administration is dependent in each individual case on the nature and severity of the condition to be treated and on the type of the compound of the formula (I) used in each case. Coated formulations and coated delayed-release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methylmethacrylate.

Suitable pharmaceutical compounds for oral administration can be present in separate units, such as, for example, capsules, cachets, lozenges or tablets, which in each case contain a specific amount of the compound of the formula (I); as a powder or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the carrier (which can consist of one or more additional constituents) are brought into contact. In general, the compositions are prepared by uniform and homogeneous mixing of the active compound with a liquid and/or finely divided solid carrier, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (number of) surface-active/dispersing agent (s) in a suitable machine. Shaped tablets can be produced by shaping the pulverulent compound moistened with an inert liquid diluent in a suitable machine.

Pharmaceutical compositions which are suitable for peroral (sublingual) administration include lozenges which contain a compound of the formula (I) with a flavoring, customarily sucrose and gum arabic or tragacanth, and pastilles which include the compound in an inert base such as gelatin and glycerol or sucrose and gum arabic.

Suitable other active compounds for the combination preparations include: all antidiabetics, mentioned in Rote Liste 2001, Chapter 12, the disclosure of which is incorporated by reference herein. They can be combined with the compounds of the formula I according to the invention in particular to achieve a synergistically enhanced action. The active compound combination can be administered either by separate administration of the active compounds to the patient or in the form of combination preparations comprising a plurality of active compounds in a pharmaceutical preparation.

Antidiabetics include insulin and insulin derivatives, such as, for example, Lantus® or HMR 1964, GLP-1 derivatives, such as, for example, those disclosed by Novo Nordisk A/S in WO 98/08871, the disclosure of which is incorporated by reference herein, and oral hypoglycemic active compounds.

The oral hypoglycemic active compounds preferably include sulphonyl ureas, biguadines, meglitinides, oxadiazolidindiones, thiazolidindiones, glucosidase inhibitors, glucagon antagonists, GLP-1 agonists, potassium channel openers, such as, for example, those disclosed by Novo Nordisk A/S in WO 97/26265 and WO 99/03861, the disclosures of which are incorporated by reference herein, insulin sensitizers, inhibitors of liver enzymes involved in stimulating gluconeogenesis and/or glycogenolysis, modulators of glucose uptake, compounds which modulate lipid metabolism, such as antihyperlipidemic active compounds and antilipidemic active compounds, compounds which reduce food intake, PPAR and PxR agonists and active compounds which act on the ATP-dependent potassium channel of the beta cells.

In one embodiment of the invention, the compounds of the formula I are administered in combination with a HMG-CoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor, such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847.

In one embodiment of the invention, the compounds of the formula I are administered in combination with a fibrate, such as, for example, fenofibrate, clofibrate, bezafibrate.

In one embodiment of the invention, the compounds of the formula I are administered in combination with an MTP inhibitor, such as, for example, Bay 13-9952, BMS-201038, R-103757.

In one embodiment of the invention, the compounds of the formula I are administered in combination with a bile acid absorption inhibitor, such as, for example, HMR 1453.

In one embodiment of the invention, the compounds of the formula I are administered in combination with a CETP inhibitor, such as, for example, Bay 194789.

In one embodiment of the invention, the compounds of the formula I are administered in combination with a polymeric bile acid adsorber, such as, for example, cholestyramine, colesolvam.

In one embodiment of the invention, the compounds of the formula I are administered in combination with an LDL receptor inducer, such as, for example, HMR 1171, HMR 1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid. In one embodiment of the invention, the compounds of the formula I are administered in combination with a lipase inhibitor, such as, for example, orlistat.

In one embodiment, of the invention the compounds of the formula I are administered in combination with insulin.

In one embodiment, the compounds of the formula I are administered in combination with a sulphonyl urea, such as, for example, tolbutamide, glibenclamide, glipizide or gliclazide.

In one embodiment, the compounds of the formula I are administered in combination with a biguanide, such as, for example, metformin.

In yet another embodiment, the compounds of the formula I are administered in combination with a meglitinide, such as, for example, repaglinide.

In one embodiment, the compounds of the formula I are administered in combination with a thiazolidindione, such as, for example, troglitazone, ciglitazone, pioglitazone, rosiglitazone, or the compounds disclosed by Dr. Reddy's Research Foundation in WO 97/41097, the disclosure of which is incorporated by reference herein, in particular 5-[[4-[(3,4-dihydro-3-methyl-4-oxo-2-quinazolinylmethoxy]phenyl]methyl]-2,4-thiazolidindione.

In one embodiment, the compounds of the formula I are administered in combination with an α-glucosidase inhibitor, such as, for example, miglitol or acarbose.

In one embodiment, the compounds of the formula I are administered in combination with an active compound which acts on the ATP-dependent potassium channel of beta cells, such as, for example, tolbutamide, glibenclamide, glipizide, gliazide or repaglinide.

In one embodiment, the compounds of the formula I are administered in combination with more than one of the abovementioned compounds, for example in combination with a sulphonyl urea and metformin, a sulphonyl urea and acarbose, repaglinide and mefformin, insulin and a sulphonyl urea, insulin and metformin, insulin and troglitazon, insulin and lovastatin, etc.

In a further embodiment, the compounds of the formula I are administered in combination with CART agonists, NPY agonists, MC4 agonists, orexin agonists, H3 agonists, TNF agonists, CRF agonists, CRF BP agonists, urocortin agonists, β3-agonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormone, growth hormone-releasing compounds, TRH agonists, decoupling protein 2- or 3 modulators, leptin agonists, DA agonists (bromocriptin, doprexin), lipase/amylase inhibitors, PPAR modulators, RxR modulators or TR-β agonists.

In one embodiment of the invention, the further active compound is leptin.

In one embodiment, the further active compound is dexamphetamine or amphetamine.

In one embodiment, the further active compound is fenfluramine or dexfenfluramine.

In yet another embodiment, the further active compound is sibutramine.

In one embodiment, the further active compound is Orlistat.

In one embodiment, the further active compound is mazindol or phentermine.

In one embodiment, the compounds of the formula I are administered in combination with fibers, preferably insoluble fibers, such as, for example, Caromax®. The combination with Caromaxe® can be given in one preparation or by separate administration of compounds of the formula I and Caromax®. Here, Caromax® can also be administered in the form of food, such as, for example, in bakery goods or muesli bars. Compared to the individual active compounds, the combination of compounds of the formula I with Caromax® is, in addition to an enhanced action, in particular with respect to the lowering of LDL cholesterol, also characterized by its improved tolerability.

It is to be understood that each suitable combination of the compounds according to the invention with one or more of the compounds mentioned above and optionally one or more further pharmacologically active substances is included in the scope of the present invention.

The invention furthermore provides both stereoisomer mixtures of the formula I and the pure stereoisomers of the formula I, and diastereomer mixtures of the formula I and the pure diastereomers. The mixtures are separated by chromatographic means.

Preference is given to both racemic and enantiomerically pure compounds of the formula I of the following structure:

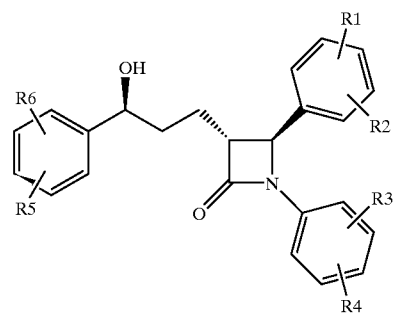

Preference is furthermore given to compounds of the formula I in which the L radicals have the following meaning:

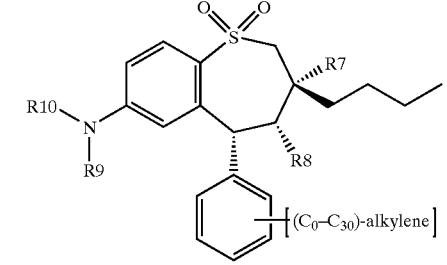

The invention furthermore provides a process for preparing the compounds of the formula I, which comprises obtaining the compounds of the formula I by proceeding analogously to the reaction scheme below.

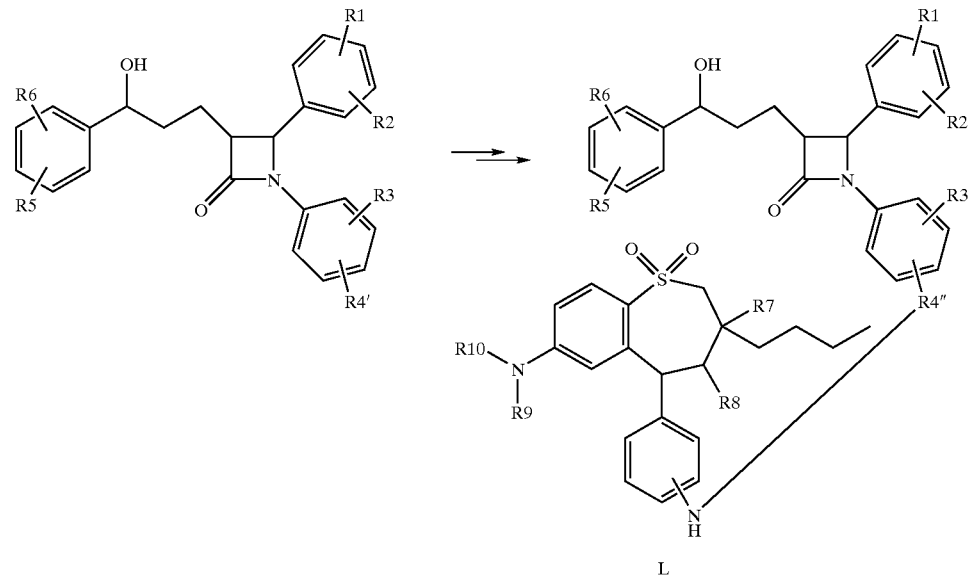

R4" is $(C_0$–$C_{30})$-alkylene in which one or more carbon atoms of the alkylene radical may be replaced by —O—, —(C═O)—, —CH═CH—, —C≡C—, —N(($C_1$–$C_6$)-alkyl)- or —NH—.

Alternatively, attachment to the L group is via ring A or ring C.

The examples below serve to illustrate the invention in more detail, without limiting the invention to the products and embodiments described in the examples.

EXAMPLE I

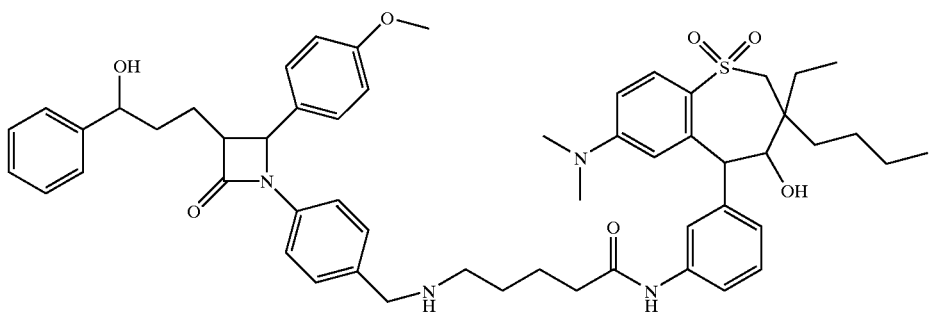

N-[3-(3-Butyl-7-dimethylamino-3-ethyl-4-hydroxy-1,1-dioxo-2,3,4,5-tetrahydro-1H-benzo[b]thiepin-5-yl)-phenyl]-5-{4-[3-(3-hydroxy-3-phenylpropyl)-2-(4-methoxyphenyl)-4-oxoazetidin-1-yl] benzylamino}pentanamide (1)

100 mg of N-[3-(3-butyl-7-dimethylamino-3-ethyl-4-hydroxy-1,1-dioxo-2,3,4,5-tetrahydro-1H-benzo[b]thiepin-5-yl)phenyl]-5-bromopentanamide and 70 mg of 1-(4-aminomethylphenyl)-3-(3-hydroxy-3-phenylpropyl)-4-(4-methoxyphenyl)azetidin-2-one are dissolved in 5 ml of dimethylformamide and, with stirring, heated at 80° C. for about 2 to 3 hours. After the reaction has ended (monitored by thin-layer chromatogram or HPLC-MS), the solvent is removed under reduced pressure and the residue is purified by chromatography. This gives product 1 of molecular weight 929.24 ($C_{55}H_{68}N_4O_7S$); MS (FAB): 929 (M+H$^+$).

EXAMPLE II

N-[3-(3-Butyl-7-dimethylamino-3-ethyl-4-hydroxy-1,1-dioxo-2,3,4,5-tetrahydro-1H-benzo[b]thiepin-5-yl)phenyl]-N'-4-[1-(4-fluorophenyl)-3-(3-hydroxy-3-phenylpropyl)-4-oxoazetidin-2-yl]benzyl-hexanediamide (8)

a) 1-(2-Oxo-4-phenyloxazolidin-3-yl)-5-phenylpentane-1,5-dione (2)

10 g of benzoylbutyric acid and 12.5 ml of triethylamine are dissolved in 55 ml of dichloromethane. After 5 min at room temperature, 6.2 ml of pivaloyl chloride are added over a period of 30 min, and the mixture is stirred for 2 hours. 5.9 g of 4-phenyloxazolidin-2-one in 6 ml of dimethylformamide and 0.9 g of 4-(dimethylamino)pyridine are then added. The mixture is heated at reflux for about 7 hours (monitored by TLC). After the reaction has ended, the mixture is put into 15 ml of 2N sulfuric acid and stirred briefly, and the phases are then separated. The org. phase is washed with 5 percent strength bicarbonate solution and, after drying, concentrating and recrystallization from ethyl acetate/n-heptane, the product of molecular weight 337.4 ($C_{20}H_{19}NO_4$); MS (DCl+): 338 (M+H$^+$), is obtained. By the same route, optically active/enantiomerically enriched 2 is obtained when optically active/enantiomerically enriched 4-phenyloxazolidin-2-one is used.

b) 3-(5-Hydroxy-5-phenylpentanoyl)-4-phenyloxazolidin-2-one (3)

Under argon and at a temperature between 0° and −5° C., 5 g of 1-(2-oxo-4-phenyloxazolidin-3-yl)-5-phenylpentane-1,5-dione in 20 ml of dichloromethane are slowly, over a period of about 3 hours, added to a solution of 1.5 ml of boron-dimethylsulfide-complex in 25 ml of dichloromethane. The mixture is stirred at the same temperature for another 2 hours, the reaction being monitored by thin-layer chromatography. After the reaction has ended, 2 ml of

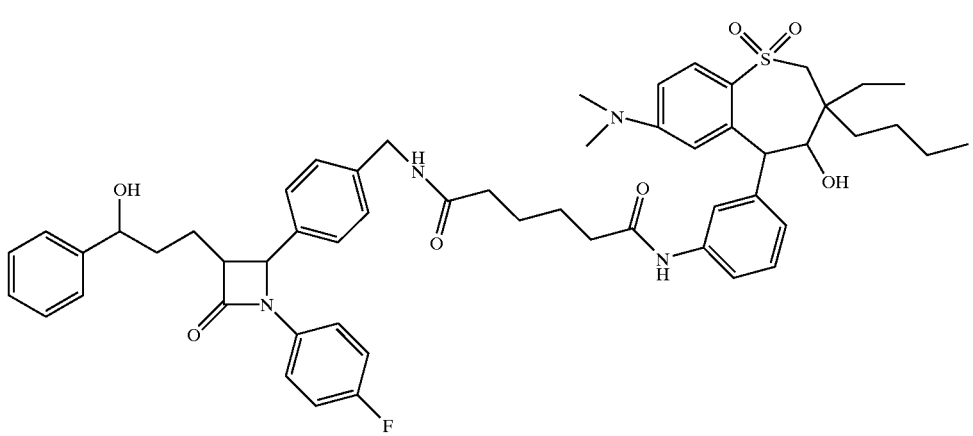

methanol and 1.5 ml of 35 percent strength hydrogen peroxide solution and 1.1 ml of 3N sulfuric acid are added at below 0° C., and the mixture is stirred at room temperature for another 15 min. After phase separation, the organic phase is washed successively with 2N sulfuric acid, 5% strength sodium bisulfite solution and 10 percent strength sodium chloride solution and then dried and concentrated. After chromatography (SiO$_2$, ethyl acetate/n-heptane=1:1, the product of molecular weight 339.4 (C$_{20}$H2$_1$NO$_4$); MS (DCl+): 322 (M+H$^+$–H$_2$O); (ESI+):403 (M+Na$^+$+CH$_3$CN), 362 (M+Na$^+$) is obtained. By adding optically active 1-methyl-3,3-diphenyltetrahydropyrrolo[1,2-c][1,3,2] oxazaborole (S or R, 0.75 ml) at from 0° to –5° C. to the reaction mixture prior to the addition of 1-(2-oxo-4-phenyloxazolidin-3-yl)-5-phenylpentane-1,5-dione, by the same route, 3 is obtained in diastereomerically enriched form.

c) 4-[1-(4-Fluorophenylamino)-2-(2-oxo-4-phenyloxazolidine-3-carbonyl)-5-phenyl-5-trimethylsilanyloxypentyl]benzonitrile (4) 3.3 g of 3-(5-hydroxy-5-phenylpentanoyl)-4-phenyloxazolidin-2-one and 3.93 g of 4-[(4-fluorophenylimino)methyl]benzonitrile, dissolved in 55 ml of dichloromethane, are cooled to –10° C., and 8.5 ml of diisopropylethylamine are added slowly. Over a period of 30 min, 5.3 ml of chlorotrimethylsilane are then added such that the temperature remains below –5° C. After one hour, the mixture is cooled to –30° C., 1.1 ml of titanium tetrachloride are added at below –25° C. and the mixture is then stirred at this temperature overnight. After the reaction has ended, 4 ml of glacial acetic acid are added dropwise at –25° C., the mixture is stirred for another 15 min, added, at 0° C., to 50 ml of 7 percent strength tartaric acid and stirred for another hour, and 25 ml of 20 percent strength sodium bisulfite solution are then added and stirring is continued for another 45 min. After phase separation, the organic phase is washed with about 40 ml of water, dried and concentrated to about 15 ml. 2.7 ml of bistrimethylsilylacetamide are then added, and the mixture is heated at reflux for 30 min. After cooling to room temperature, the mixture is concentrated, giving, after crystallization of the residue from ethyl acetate/n-heptane, the product of molecular weight 635.8 (C$_{37}$H$_{38}$FN$_3$O$_4$Si); MS (ESI+): 636 (M+H$^+$).

d) 4-[1-(4-Fluorophenyl)-3-(3-hydroxy-3-phenylpropyl)-4-oxo-azetidin-2-yl]benzonitrile (5)

2.7 g of 4-[1-(4-fluorophenylamino)-2-(2-oxo-4-phenyloxazolidine-3-carbonyl)-5-phenyl-5-trimethylsilanyloxypentyl]benzonitrile in 30 ml of tert-butyl methyl ether, 1.6 ml of bistrimethylsilylacetamide and 0.2 g of tetrabutylammonium fluoride trihydrate are heated at reflux for 3 hours. The mixture is allowed to stand overnight, 0.2 ml of glacial acetic acid are added, and the mixture is stirred for 15 min and then substantially concentrated. 15 ml of a mixture of isopropanol/2N sulfuric acid=10:1 are added, and the mixture is stirred at room temperature for 1 hour. The mixture is then treated with a little solid sodium bicarbonate and again substantially concentrated and the residue is taken up in ethyl acetate and washed with water. The residue of the dried organic phase is purified by column filtration (SiO$_2$, ethyl acetate/n-heptane=1:1). This gives the product of molecular weight 400.5 (C$_{25}$H$_{21}$FN$_2$O$_2$); MS (DCl+): 401 (M+H$^+$), 383 (M+H$^+$–H$_2$O).

e) 4-(4-Aminomethylphenyl)-1-(4-fluorophenyl)-3-(3-hydroxy-3-phenylpropyl)-azetidin-2-one (6)

930 mg of 4-[1-(4-fluorophenyl)-3-(3-hydroxy-3-phenylpropyl)-4-oxo-azetidin-2-yl]-benzonitrile, dissolved in 100 ml of ethanol, are admixed with 4 ml of conc. ammonia and hydrogenated for 20 hours over Raney Ni, at room temperature and a hydrogen pressure of 20 bar. The catalyst is filtered off and the filtrate is concentrated under reduced pressure, giving, after chromatography (SiO$_2$, dichloromethane/methanol=0:1), the product of molecular weight 404.5 (C$_{25}$H$_{25}$FN$_2$O$_2$); MS (DCl+): 405 (M+H$^+$), 387 (M+H$^+$–H$_2$O).

f) 5-[3-(3-Butyl-7-dimethylamino-3-ethyl-4-hydroxy-1,1-dioxo-2,3,4,5-tetrahydro-1H-benzo[b]thiepin-5-yl)-phenylcarbamoyl]pentanoic Acid (7)

2 g of 5-(3-aminophenyl)-3-butyl-7-dimethylamino-3-ethyl-1,1-dioxo-2,3,4,5-tetra-hydro-1H-benzo[b]thiepin-4-ol, 3.4 g of hexanedioic acid, 1.04 g of dicyclohexylcarbodiimide and 640 mg of benzotriazol-1-ol in 80 ml of tetrahydrofuran are stirred at room temperature overnight. The mixture is concentrated, the residue is taken up in ethyl acetate, excess urea is removed by filtration and the mixture is washed with water. The residue of the dried organic phase is purified by column filtration (SiO$_2$, dichloromethane/methanol=20:1). This gives the product of molecular weight 558.7 (C$_{30}$H$_{42}$N$_2$O$_6$S); MS (ESI+): 559 (M+H$^+$).

g) N-[3-(3-Butyl-7-dimethylamino-3-ethyl-4-hydroxy-1,1-dioxo-2,3,4,5-tetrahydro-1H-benzo[b]thiepin-5-yl)phenyl]-N'-4-[1-(4-fluorophenyl)-3-(3-hydroxy-3-phenylpropyl)-4-oxoazetidin-2-yl]benzyl-hexanediamide (8)

83 mg of 4-(4-aminomethylphenyl)-1-(4-fluorophenyl)-3-(3-hydroxy-3-phenylpropyl)-azetidin-2-one, 115 mg of 5-[3-(3-butyl-7-dimethylamino-3-ethyl-4-hydroxy-1,1-dioxo-2,3,4,5-tetrahydro-1H-benzo[b]thiepin-5-yl) phenylcarbamoyl]pentanoic acid, 45 mg of dicyclohexylcarbodiimide and 35 mg of benzotriazol-1-ol in 5 ml of tetrahydrofuran are stirred at room temperature overnight. The mixture is concentrated under reduced pressure giving, after chromatography (SiO$_2$, dichloromethane/methanol= 20:1), the product of melting point 150° C. and molecular weight 945.2 (C$_{55}$H$_{65}$FN$_4$O$_7$S); MS (ESI+): 945 (M+H$^+$).

EXAMPLE III

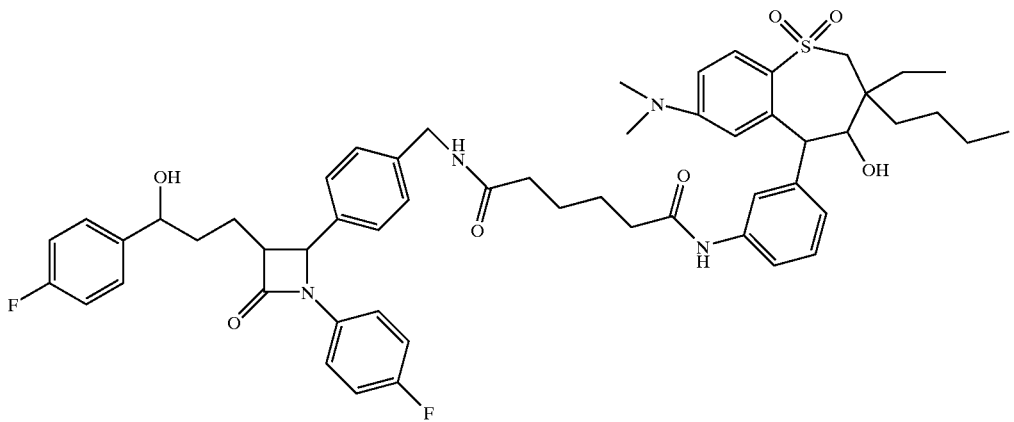

N-[3-(3-Butyl-7-dimethylamino-3-ethyl-4-hydroxy-1,1-dioxo-2,3,4,5-tetrahydro-1H-benzo[b]thiepin-5-yl)phenyl]-N'-4-{1-(4-fluorophenyl)-3-[3-(4-fluorophenyl)-3-hydroxypropyl]-4-oxo-azetidin-2-yl}benzyl-hexanediamide (12)

a) 4-[5-(4-Fluorophenyl)-1-(4-fluorophenylamino)-2-(2-oxo-4-phenyloxazolidine-3-carbonyl)-5-trimethylsilanyloxypentyl]benzonitrile (9)

Preparation analogous to example 11 using 3-[5-(4-fluorophenyl)-5-hydroxypentanoyl]-4-phenyloxazolidin-2-one The product of molecular weight 653.8 ($C_{37}H_{37}F_2N_3O_4Si$); MS (ESI+): 654 (M+H$^+$).

b) 4-{1-(4-Fluorophenyl)-3-[3-(4-fluorophenyl)-3-hydroxypropyl]-4-oxo-azetidin-2-yl}-benzonitrile (10)

Preparation analogous to example II, using 4-[5-(4-fluorophenyl)-1-(4-fluorophenylamino)-2-(2-oxo-4-phenyloxazolidin-3-carbonyl)-5-trimethylsilanyloxypentyl]benzo-nitrile; product of molecular weight 418.5 ($C_{25}H_{20}F_2N_2O_2$); MS (ESI+): 419 (M+H$^+$).

c) 4-(4-Aminomethylphenyl)-1-(4-fluorophenyl)-3-[3-(4-fluorophenyl)-3-hydroxypropyl]-azetidin-2-one (11)

Preparation analogous to example II; using 4-{1-(4-fluorophenyl)-3-[3-(4-fluorophenyl)-3-hydroxypropyl]-4-oxo-azetidin-2-yl}benzonitrile; product of molecular weight 422.5 ($C_{25}H_{24}F_2N_2O_2$); MS (ESI+): 423 (M+H$^+$).

d) N-[3-(3-Butyl-7-dimethylamino-3-ethyl-4-hydroxy-1,1-dioxo-2,3,4,5-tetrahydro-1H-benzo[b]thiepin-5-yl)phenyl]-N'-4-{1-(4-fluorophenyl)-3-[3-(4-fluorophenyl)-3-hydroxpropyl]-4-oxoazetidin-2-yl}benzyl-hexanediamide (12)

Preparation analogous to example 11; product of molecular weight 963.2 ($C_{55}H_{64}F_2N_4O_7S$); MS (ESI+): 963 (M+H$^+$).

EXAMPLE V

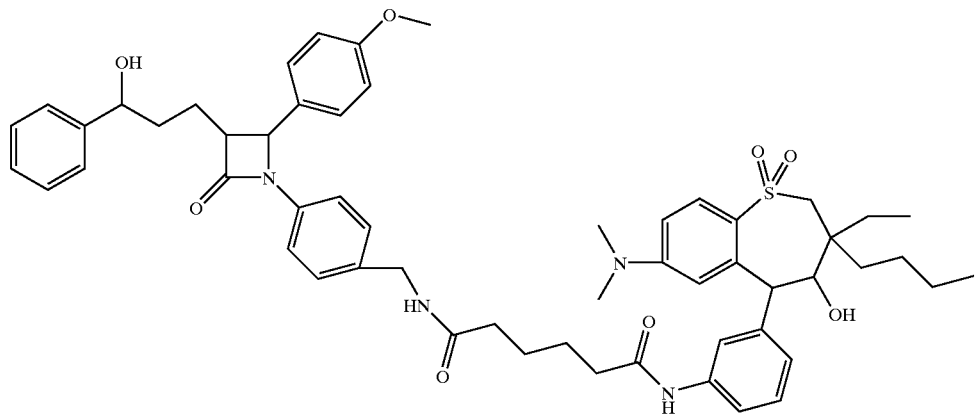

N-[3-(3-Butyl-7-dimethylamino-3-ethyl-4-hydroxy-1,1-dioxo-2,3,4,5-tetrahydro-1H-benzo[b]thiepin-5-yl)phenyl]-N'-4-[3-(3-hydroxy-3-phenylpropyl)-2-(4-methoxyphenyl)-4-oxo-azetidin-1-yl]benzyl-hexanediamide (15)

Preparation analogous to example III, starting from 1-(4-aminomethylphenyl)-3-(3-hydroxy-3-phenylpropyl)-4-(4-methoxyphenyl)azetidin-2-one; product of molecular weight 957.2 ($C_{56}H_{68}N_4O_8S$); MS (ESI+): 957 (M+H$^+$).

EXAMPLE VI

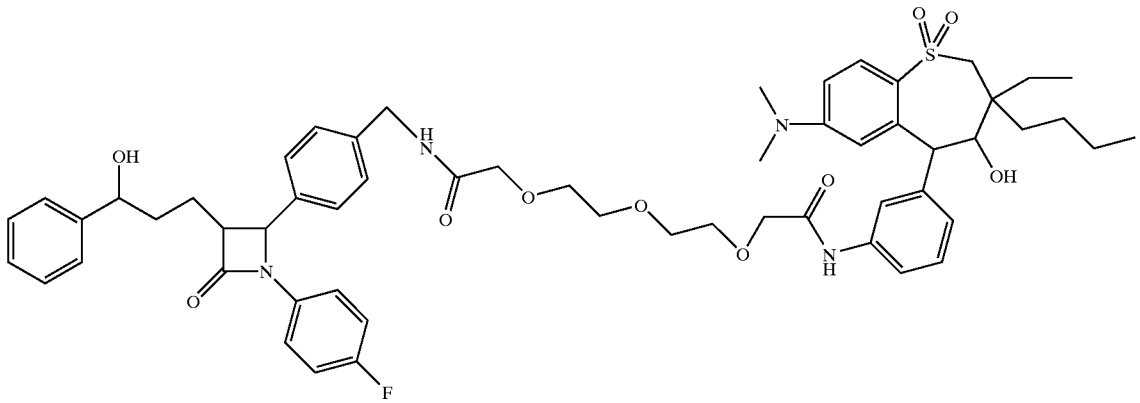

[2-(2-{[3-(3-Butyl-7-dimethylamino-3-ethyl-4-hydroxy-1,1-dioxo-2,3,4,5-tetrahydro-1H-benzo[b]thiepin-5-yl)-phenylcarbamoyl]methoxy}ethoxy)ethoxy]-[N-{4-[1-(4-fluorophenyl)-3-(3-hydroxy-3-phenylpropyl)-4-oxoazetidin-2-yl]benzyl}]acetamide (16)

Preparation analogous to example II, starting from 83 mg of 4-(4-aminomethylphenyl)-1-(4-fluorophenyl)-3-(3-hydroxy-3-phenylpropyl)azetidin-2-one and 130 mg of [2-(2-{[3-(3-butyl-7-dimethylamino-3-ethyl-4-hydroxy-1,1-dioxo-2,3,4,5-tetrahydro-1H-benzo[b]thiepin-5-yl)phenylcarbamoyl]methoxy}ethoxy)ethoxy]acetic acid; chromatography: $SiO_2$, dichloromethane/methanol=20:1; product of melting point 120° C. and molecular weight 1021.3 ($C_{57}H_{67}FN_4O_{10}S$); MS (ESI+): 1021 (M+H$^+$).

EXAMPLE VII dioxo-2,3,4,5-tetrahydro-1H-benzo[b]thiepin-5-yl)-phenylcarbamoyl]methoxy}ethoxy)acetic Acid (17)

Over a period of 2 h, 500 mg of 5-(3-aminophenyl)-3-butyl-7-dimethylamino-3-ethyl-1,1-dioxo-2,3,4,5-tetrahydro-1H-1-benzo[b]thiepin-4-ol in 8 ml of THF are added dropwise to a solution of 965 mg of 3,6-dioxooctanedioic acid, 188 mg of hydroxybenzotriazole and 287 mg of dicyclohexylcarbodiimide in 10 ml of tetrahydrofuran (THF). The mixture is stirred at room temperature for 12 h. The reaction solution is concentrated, taken up in 2 N hydrochloric acid and extracted with ethyl acetate. The organic phase is dried over magnesium sulfate, concentrated and purified by HPLC (Merck-Hibar-Lichrospher 100-RP-18, water (0.1% trifluoroacetic acid)/acetonitrile (0.1% trifluoroacetic acid)=80/20→10/90). This gives 17.

$C_{30}H_{41}N_2O_8S_1$ (590.74) MS (ESI) 592 (M+H).

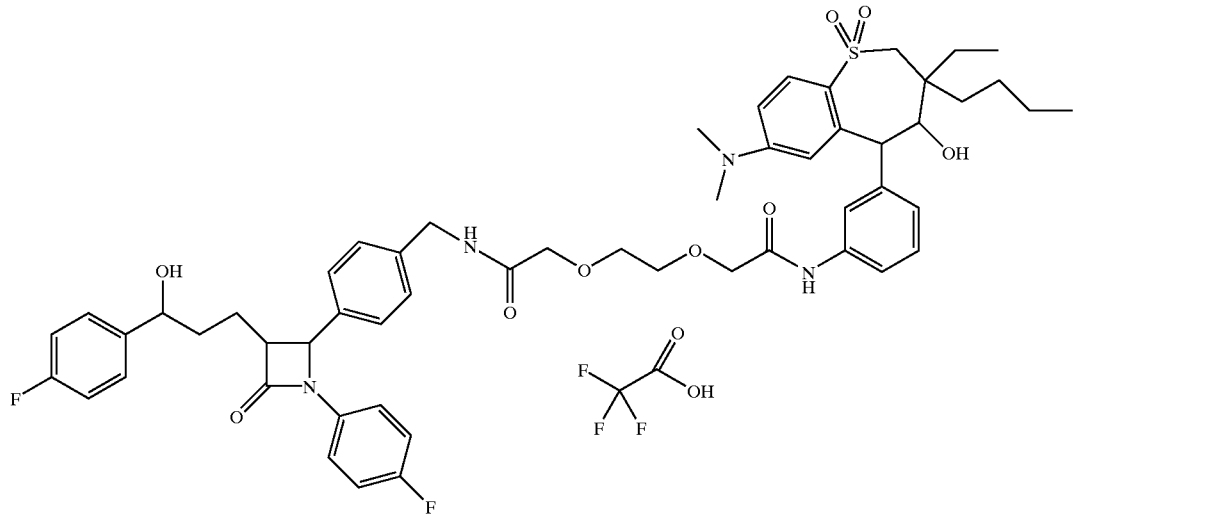

(3-Butyl-3-ethyl-5-[3-(2-{2-[(4-{1-(4-fluorophenyl)-3-[3-(4-fluorophenyl)-3-hydroxypropyl]-4-oxoazetidin-2-yl}benzylcarbamoyl)methoxy]ethoxy}acetylamino)phenyl]-4-hydroxy-1,1-dioxo-2,3,4,5-tetrahydro-1H-benzo[b]thiepin-7-yl)dimethylammonium; Trifluoroacetate (18)

a) (2-{[3-(3-Butyl-7-dimethylamino-3-ethyl-4-hydroxy-1,1-

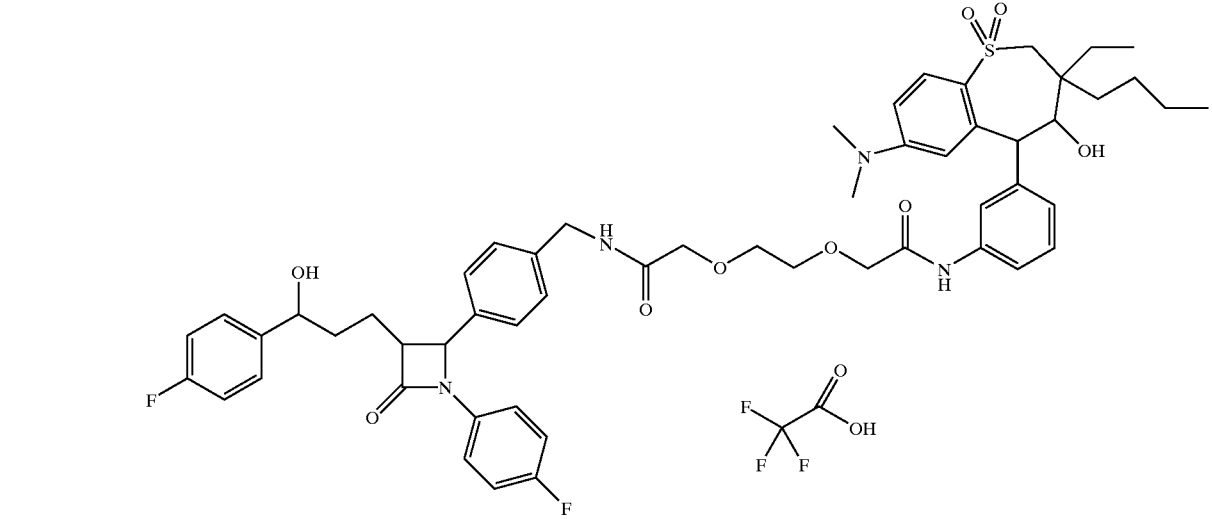

b) (3-Butyl-3-ethyl-5-[3-(2-{2-[(4-{1-(4-fluorophenyl)-3-[3-(4-fluorophenyl)-3-hydroxypropyl]-4-oxo-azetidin-2-yl}-benzylcarbamoyl )methoxy]ethoxy}acetylamino)phenyl]-4-hydroxy-1,1-dioxo-2,3,4,5-tetrahydro-1H-benzo[b]thiepin-7-yl)dimethylammonium; Trifluoroacetate (18)

A solution of 100 mg of 4-(4-aminomethylphenyl)-1-(4-fluorophenyl)-3-[3-(4-fluorophenyl)-3-hydroxypropyl]azetidin-2-one, 209 mg of (2-{[3-(3-butyl-7-dimethylamino-3-ethyl-4-hydroxy-1,1-dioxo-2,3,4,5-tetrahydro-1H-benzo[b]thiepin-5-yl)-phenylcarbamoyl]methoxy}ethoxy)acetic acid, 93 µl of diisopropylcarbodiimide and 65 mg of hydroxybenzotriaz-ole in 2 ml of methylene chloride is stirred at room temperature for 12 h. Water is added, and the mixture is extracted with methylene chloride. The organic phase is dried over magnesium sulfate and concentrated, and the residue is separated by HPLC (Knauer Eurospher-100-10-C18, water (0.1% trifluoroacetic acid)/acetonitrile (0.1% trifluoroacetic acid)=80/20→10/90). This gives 18.

$C_{57}H_{63}F_5N_4O_{11}S_1$ (1109.23) MS (ESI) 977 (M+H−H$_2$O).

Examples (VIII–XXIV) below are prepared analogously to example VII:

EXAMPLE VIII

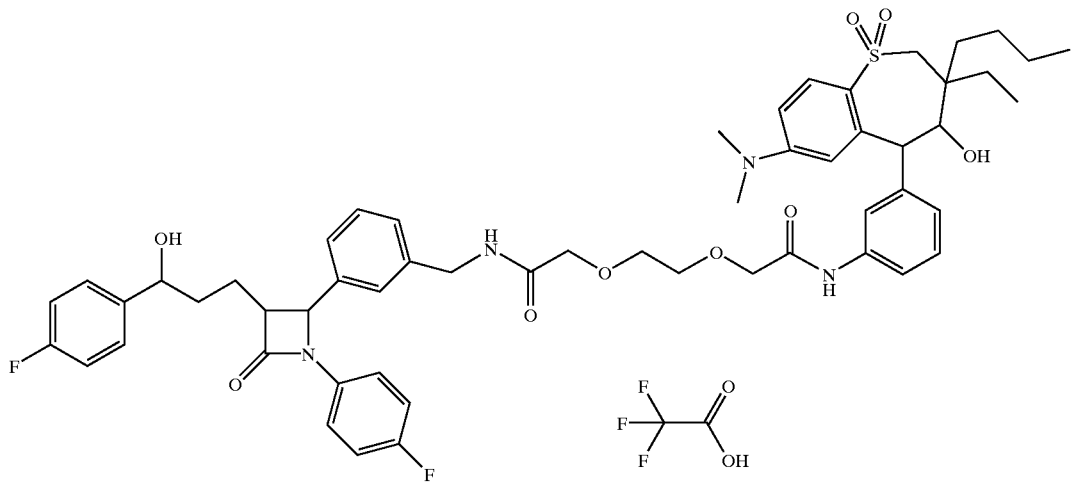

(3-Butyl-3-ethyl-5-[3-(2-{2-[(3-{1-(4-fluorophenyl)-3-[3-(4-fluorophenyl)-3-hydroxypropyl]-4-oxoazetidin-2-yl}benzylcarbamoyl)methoxy]ethoxy}acetylamino)phenyl]-4-hydroxy-1,1-dioxo-2,3,4,5-tetrahydro-1H-benzo[b]thiepin-7-yl)dimethylammonium Trifluoroacetate (19)

$C_{57}H_{65}F_5N_4O_{11}S_1$ (1109.23) MS (ESI) 977 (M+H−H$_2$O).

EXAMPLE IX

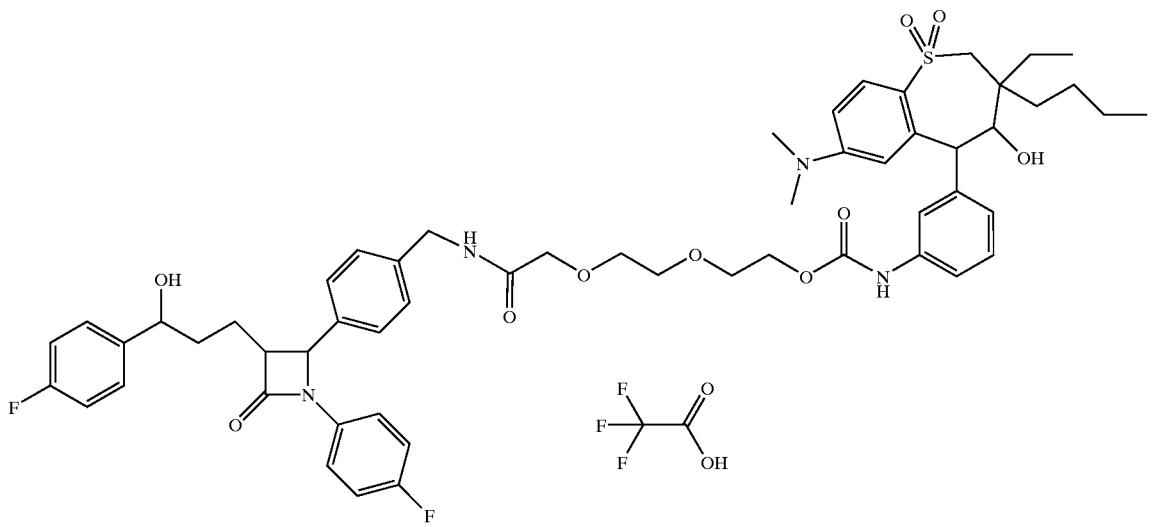

3-Butyl-3-ethyl-5-{3-[2-(2-{2-[(4-{1-(4-fluorophenyl)-3-[3-(4-fluorophenyl)-3-hydroxypropyl]-4-oxoazetidin-2-yl}benzylcarbamoyl)methoxy]ethoxy}ethoxy)acetylamino]-phenyl}-4-hydroxy-1,1-dioxo-2,3,4,5-tetrahydro-1H-benzo[b]thiepin-7-yl) dimethylammonium Trifluoroacetate (21)

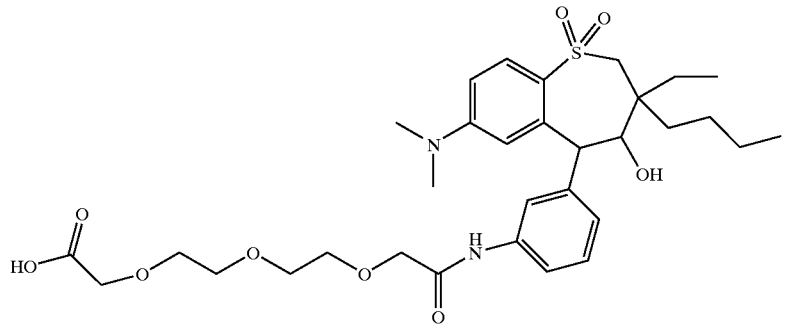

a) [2-(2-{[3-(3-Butyl-7-dimethylamino-3-ethyl-4-hydroxy-1,1-dioxo-2,3,4,5-tetrahydro-1H-benzo[b]thiepin-5-yl)-phenylcarbamoyl]methoxy}ethoxy)ethoxy]acetic Acid (20)

$C_{32}H_{46}N_2O_3S_1$ (634.3) MS (ESI) 635 (M+H).

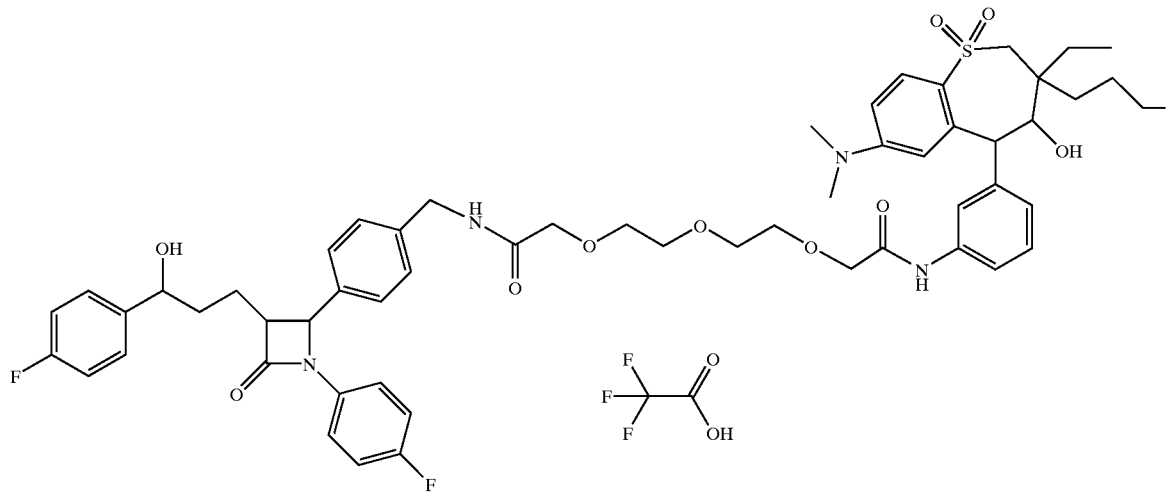

b) (3-Butyl-3-ethyl-5-{3-[2-(2-{2-[(4-{1-(4-fluorophenyl)-3-[3-(4-fluorophenyl)-3-hydroxypropyl]-4-oxoazetidin-2-yl}benzylcarbamoyl)methoxy]ethoxy}ethoxy)acetylamino]phenyl}-4-hydroxy-1,1-dioxo-2,3,4,5-tetrahydro-1H-benzo[b]thiepin-7-yl)-dimethylammonium Trifluoroacetate (21)

$C_{59}H_{69}F_5N_4O_{12}S_1$ (1153.28) MS (ESI) 1039 (M+H).

EXAMPLE X

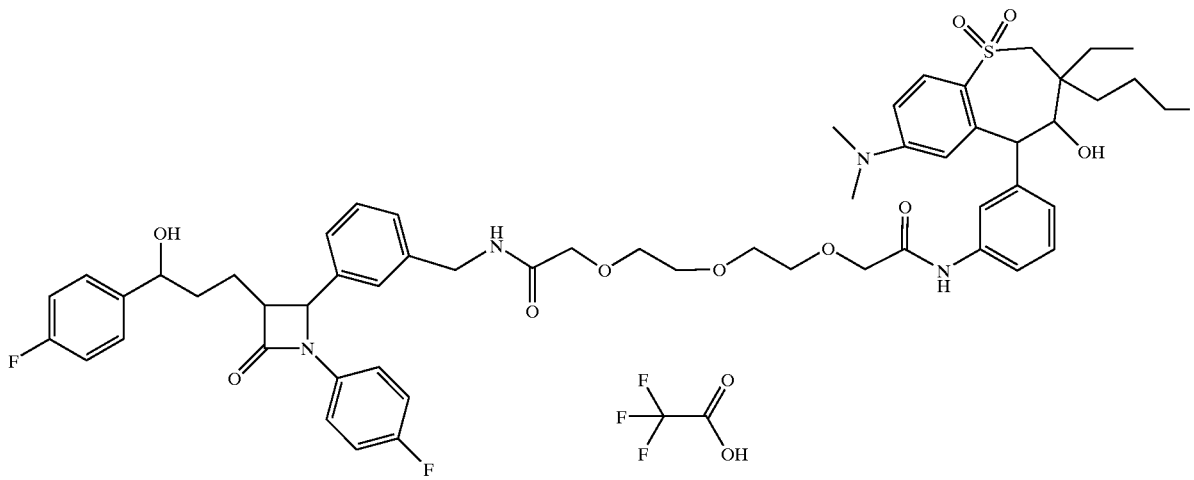

(3-Butyl-3-ethyl-5-{3-[2-(2-{2-[(3-{1-(4-fluorophenyl)-3-[3-(4-fluorophenyl)-3-hydroxypropyl]-4-oxoazetidin-2-yl}benzylcarbamoyl)methoxy]ethoxy}ethoxy)acetylamino]-phenyl}-4-hydroxy-1,1-dioxo-2,3,4,5-tetrahydro-1H-benzo[b]thiepin-7-yl)-dimethylammonium Trifluoroacetate (22)

$C_{59}H_{69}F_5N_4O_{12}S_1$ (1153.28) MS (ESI) 1040 (M+H).

EXAMPLE XI

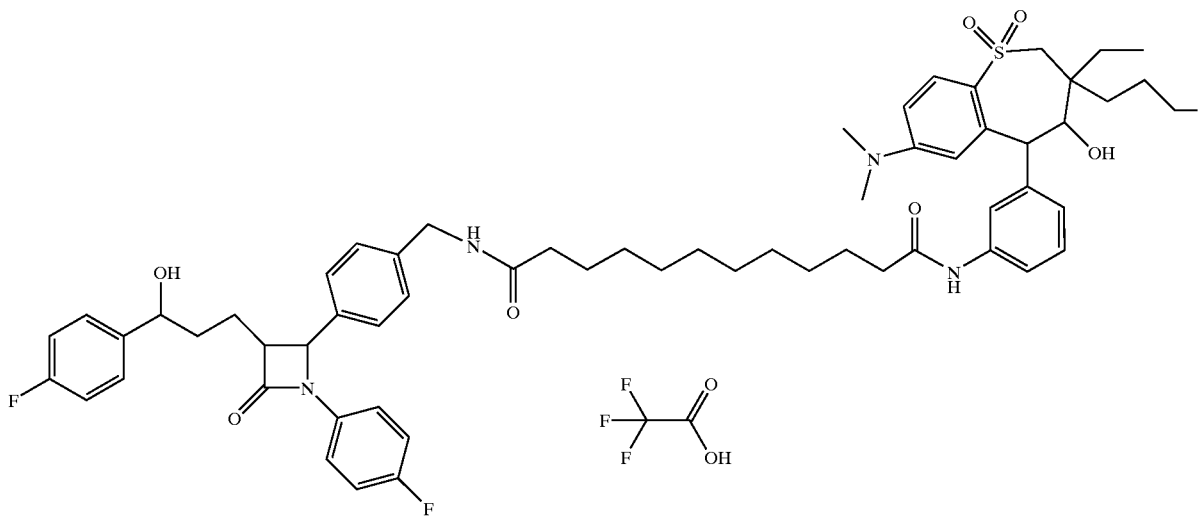

(3-Butyl-3-ethyl-5-{3-[11-(4-{1-(4-fluorophenyl)-3-[3-(4-fluorophenyl)-3-hydroxypropyl]-4-oxoazetidin-2-yl}benzylcarbamoyl)undecanoylamino]phenyl}-4-hydroxy-1,1-dioxo-2,3,4,5-tetrahydro-1H-benzo[b]thiepin-7-yl)dimethylammonium Trifluoroacetate (24)

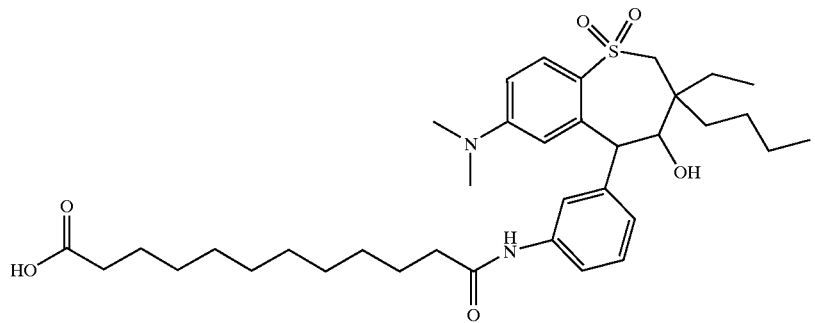
a) 11-[3-(3-Butyl-7-dimethylamino-3-ethyl-4-hydroxy-1,1-dioxo-2,3,4,5-tetrahydro-1H-benzo[b]thiepin-5-yl)phenylcarbamoyl]undecanoic Acid (23)
$C_{36}H_{54}N_2O_6S_1$ (642.91) MS (ESI) 643 (M+H).
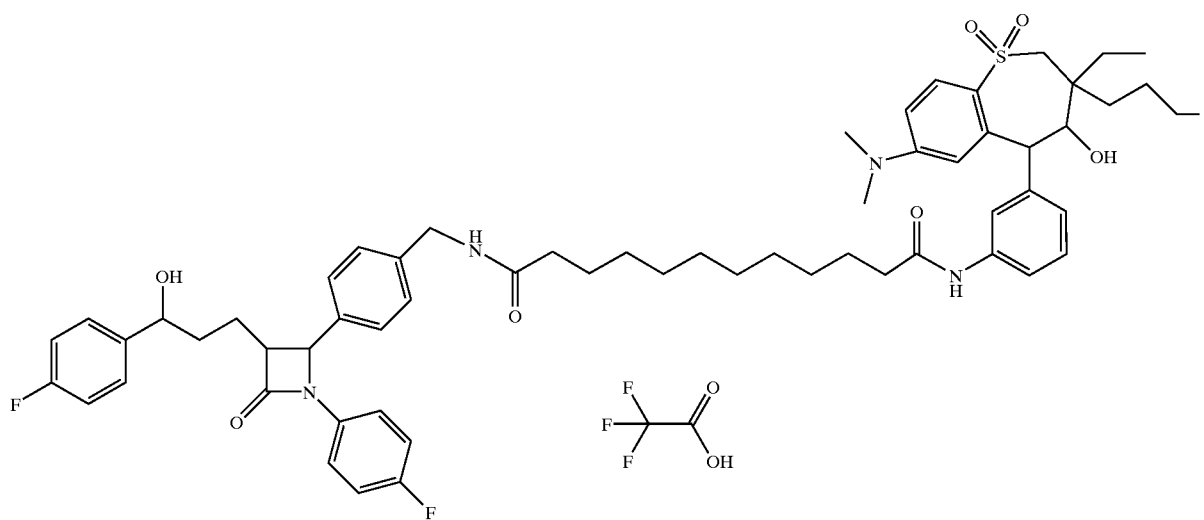
b) (3-Butyl-3-ethyl-5-{3-[11-(4-{1-(4-fluorophenyl)-3-[3-(4-fluorophenyl)-3-hydroxypropyl]-4-oxoazetidin-2-yl}benzylcarbamoyl)undecanoylamino]phenyl}-4-hydroxy-1,1-dioxo-2,3,4,5-tetrahydro-1H-benzo[b]thiepin-7-yl)dimethylammonium Trifluoroacetate (24)
$C_{63}H_{77}F_5N_4O_9S_1$ (1161.39) MS (ESI) 1047 (M+H).
EXAMPLE XII
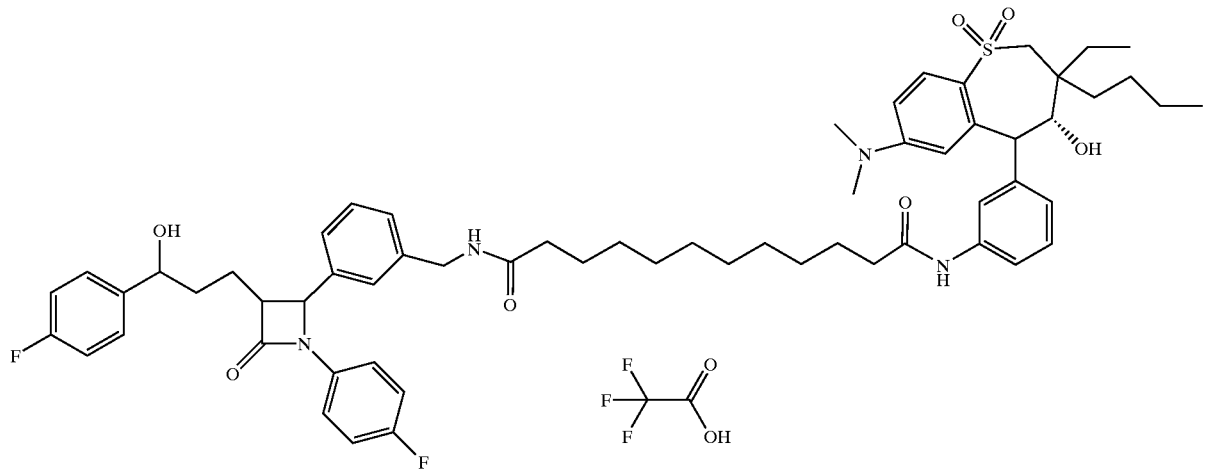

(3-Butyl-3-ethyl-5-{3-[11-(3-{1-(4-fluorophenyl)-3-[3-(4-fluorophenyl)-3-hydroxypropyl]-4-oxoazetidin-2-yl}benzylcarbamoyl)undecanoylamino]phenyl}-4-hydroxy-1,1-dioxo-2,3,4,5-tetrahydro-1H-benzo[b]thiepin-7-yl)dimethylammonium Trifluoro-acetate (25)

$C_{63}H_{77}F_5N_4O_9S_1$ (1161.39) MS (ESI) 1047 (M+H).

EXAMPLE XXI

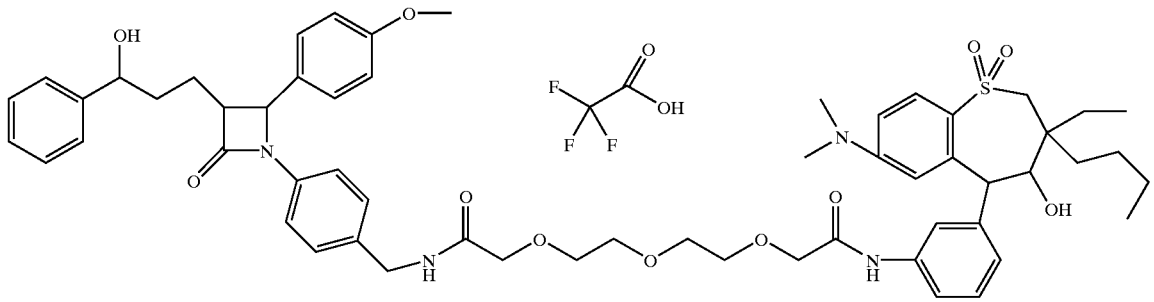

(3-Butyl-3-ethyl-5-{3-[2-(2-{2-[(4-[3-(3-hydroxy-3-phenylpropyl)-2-(4-methoxyphenyl)-4-oxoazetidin-1-yl]benzylcarbamoyl)methoxy]ethoxy}ethoxy)acetylamino]phenyl}-4-hydroxy-1,1-dioxo-2,3,4,5-tetrahydro-1H-benzo[b]thiepin-7-yl)dimethylammonium Trifuoroacetate (38)

$C_{60}H_{73}F_3N_4O_{13}S_1$ (1147.33) MS (ESI) 1033 (M+H).

EXAMPLE XXII

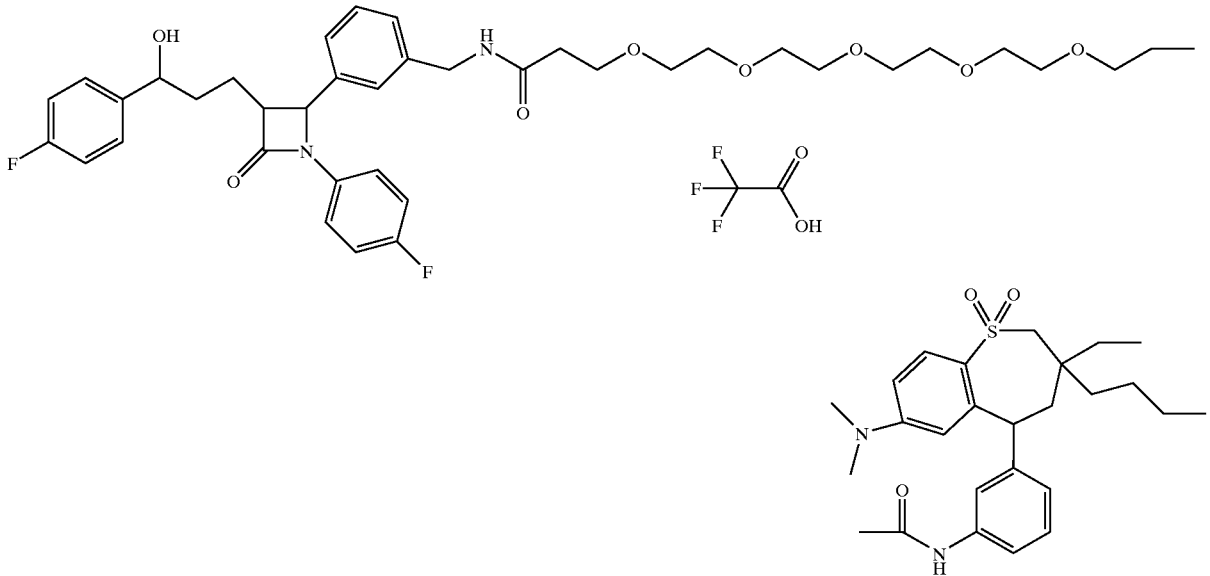

{3-Butyl-3-ethyl-5-[3-(3-{2-[2-(2-{2-[2-(3-{1-(4-fluorophenyl)-3-[3-(4-fluorophenyl)-3-hydroxypropyl]-4-oxoazetidin-2-yl}benzylcarbamoyl)ethoxy]ethoxy}ethoxy)ethoxy]ethoxy}propionylamino)phenyl]-4-hydroxy-1,1-dioxo-2,3,4,5-tetrahydro-1H-benzo[b]-thiepin-7-yl}dimethylammonium Trifluoroacetate (42)

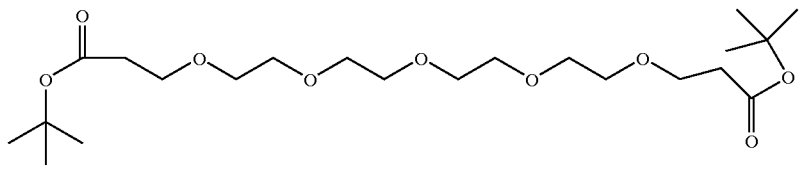

a) tert-Butyl 3-[2-(2-{2-[2-(2-tert-butoxycarbonylethoxy) ethoxy]ethoxy}ethoxy)-ethoxy]propionate (39)

0.4 g of sodium is added to a solution of 91 g of tetraethylene glycol in 250 ml of tetrahydrofuran, and the mixture is stirred at room temperature. Once the sodium has dissolved, 145 ml of tert-butyl acrylate are added. The mixture is stirred for 12 h. The reaction solution is neutralized with ammonium chloride, concentrated, taken up in aqueous sodium chloride solution and extracted with ethyl acetate. The organic phase is concentrated. The residue is 39.

$C_{22}H_{42}O_9$ (450.57) MS (ESI) 339 (M+3*H−2* tert-Bu)

b) 3-[2-(2-{2-[2-(2-Carboxyethoxy)ethoxy]ethoxy}ethoxy) ethoxy]propionic Acid (40)

A solution of tert-butyl 3-[2-(2-{2-[2-(2-tert-butoxycarbonylethoxy)ethoxy]ethoxy}-ethoxy)ethoxy] propionate 24 in 50 ml of methylene chloride and 50 ml of trifluoroacetic acid is stirred for 2 h and then concentrated. The residue is taken up in 1N hydrochloric acid and extracted with methylene chloride. The organic phase is concentrated and contains 40.

$C_{14}H_{26}O_9$ (338.36) MS (ESI) 339 (M+H).

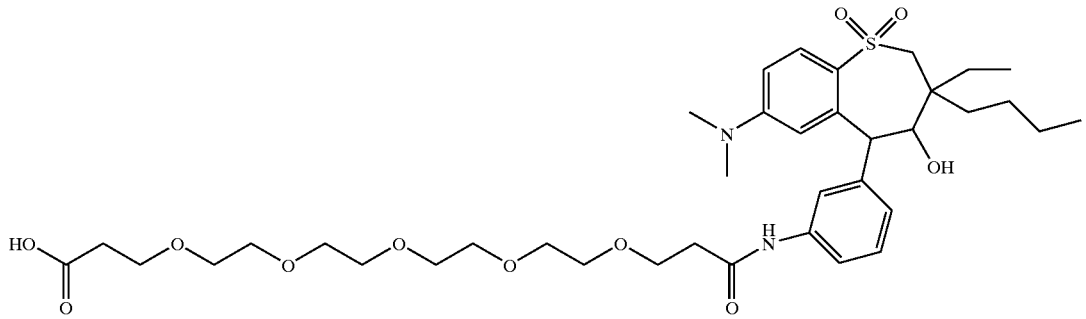

c) 3-(2-{2-[2-(2-{2-[3-(3-Butyl-7-dimethylamino-3-ethyl-4-hydroxy-1,1-dioxo-2,3,4,5-tetrahydro-1H-benzo[b] thiepin-5-yl)phenylcarbamoyl]ethoxy}ethoxy)ethoxy] ethoxy}-ethoxy)propionic Acid (41)

The synthesis is carried out analogously to 17.

$C_{39}H_{60}N_2O_{11}S_1$ (750.97) MS (ESI) 751 (M+H).

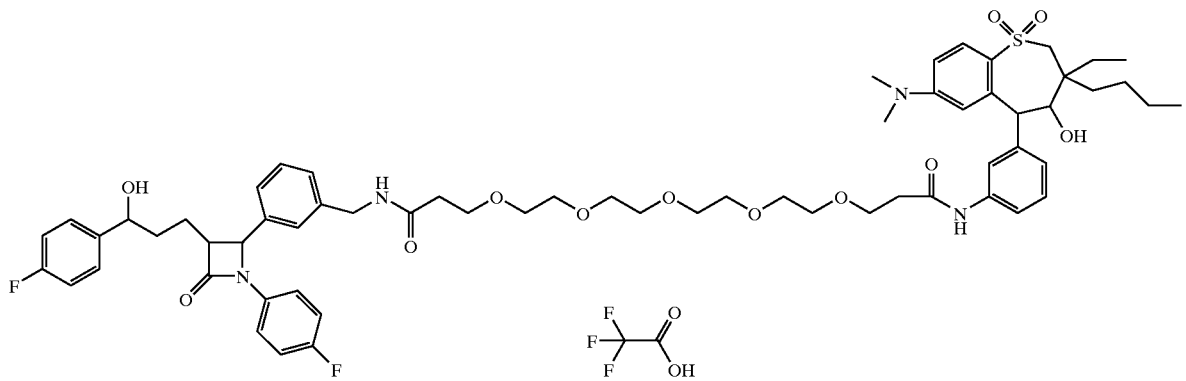

d) {3-Butyl-3-ethyl-5-[3-(3-{2-[2-(2-{2-[2-(3-{1-(4-fluorophenyl)-3-[3-(4-fluorophenyl)-3-hydroxypropyl]-4-oxoazetidin-2-yl}benzylcarbamoyl)ethoxy]ethoxy}ethoxy)-ethoxy]ethoxy}propionylamino)phenyl]-4-hydroxy-1,1-dioxo-2,3,4,5-tetrahydro-1H-benzo[b]thiepin-7-yl}dimethylammonium Trifluoroacetate (42)

$C_{65}H_{81}F_5N_4O_{14}S_1$ (1269.44) MS (ESI) 1155 (M+H).

EXAMPLE XXIII

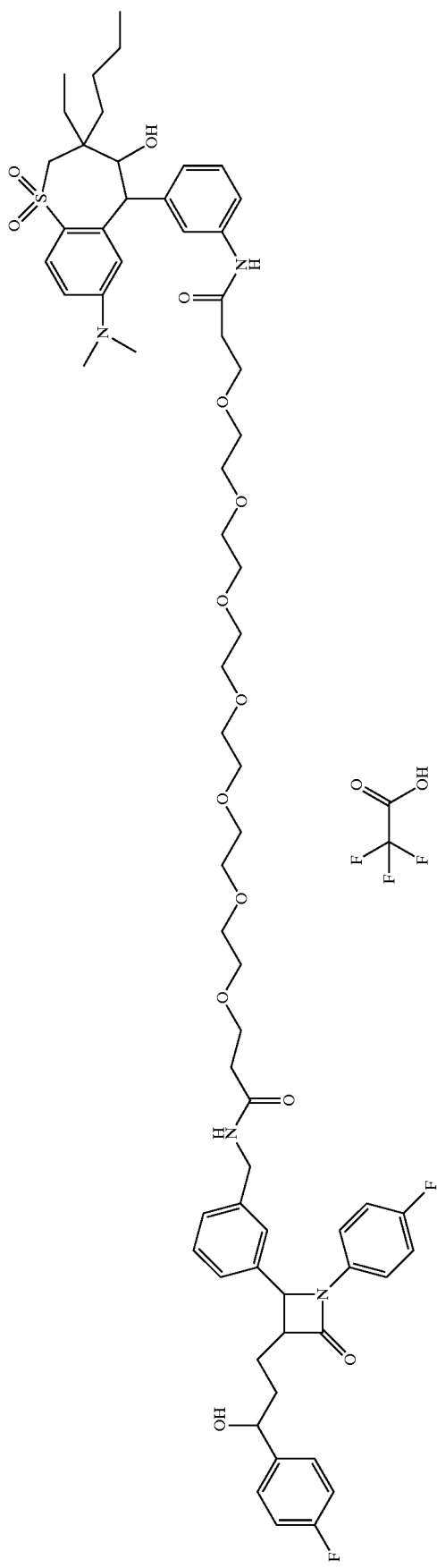

[3-Butyl-3-ethyl-5-(3-{3-[2-(2-{2-[2-(2-{2-[2-{3-[1-(4-fluorophenyl)-3-[3-(4-fluorophenyl)-3-hydroxypropyl]-4-oxo-azetidin-2-yl]benzylcarbamoyl}ethoxy]ethoxy}ethoxy)ethoxy]ethoxy}ethoxy)ethoxy]propionylamino}phenyl)-4-hydroxy-1,1-dioxo-2,3,4,5-tetrahydro-1H-benzo[b]thiepin-7-yl]dimethylammonium Trifluoroacetate (46)

a) tert-Butyl 3-(2-{2-[2-(2-{2-[2-(2-tert-Butoxycarbonylethoxy)ethoxy]ethoxy}ethoxy]ethoxy}ethoxy)propionate (43)

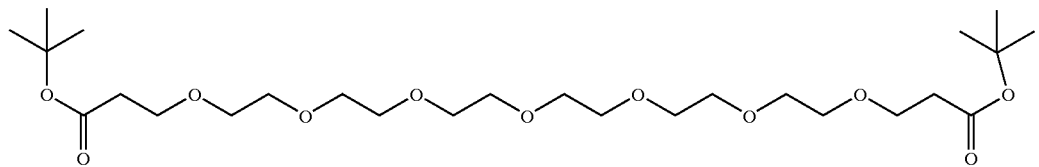

The synthesis is carried out analogously to 39.
$C_{26}H_{50}O_{11}$ (538.68) MS (ESI) 427 (M+3*H−2* tert-Bu).

b) 3-(2-{2-[2-(2-{2-[2-(2-Carboxyethoxy)ethoxy]ethoxy}ethoxy)ethoxy]ethoxy}ethoxy)propionic Acid (44)

The synthesis is carried out analogously to 40.
$C_{18}H_{34}O_{11}$ (426.47) MS (ESI) 427 (M+H).

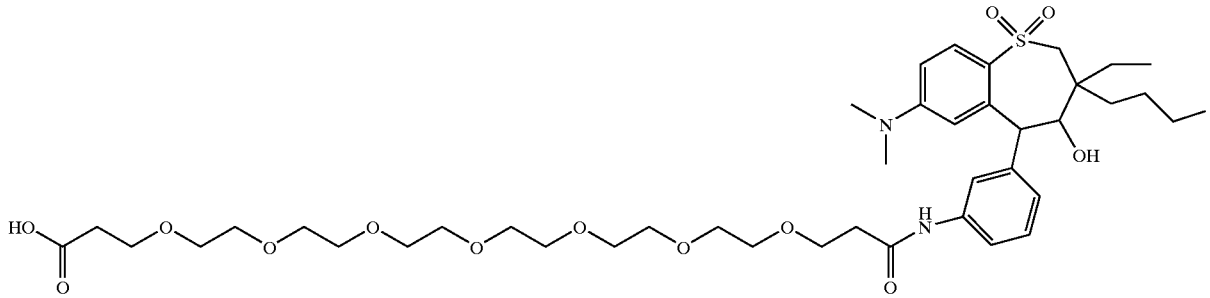

c) 3-{2-[2-(2-{2-[2-(2-{2-[3-(3-Butyl-7-dimethylamino-3-ethyl-4-hydroxy-1,1-dioxo-2,3,4,5-tetrahydro-1H-benzo[b]thiepin-5-yl)phenylcarbamoyl]ethoxy}ethoxy)ethoxy]ethoxy}ethoxy)ethoxy]ethoxy}propionic Acid (45)

The synthesis is carried out analogously to 17.
$C_{43}H_{66}N_2O_3S_1$ (839.09) MS (ESI) 840 (M+H).

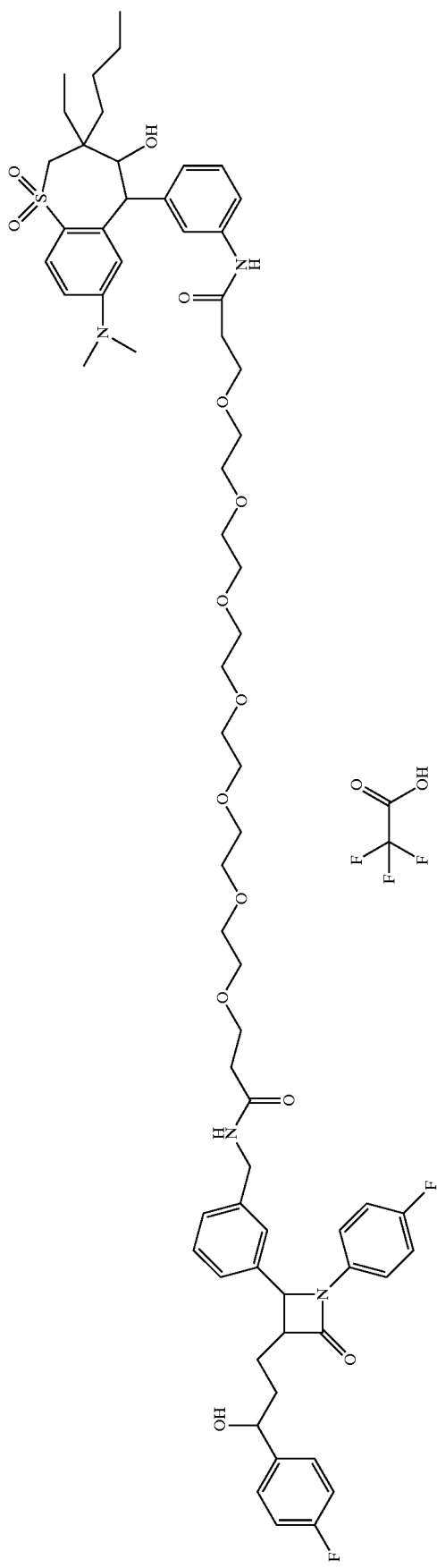

d) [3-Butyl-3-ethyl-5-(3-{3-[2-(2-{2-[2-(2-{2-[2-{3-[1-(4-fluorophenyl)-3-[3-(4-fluorophenyl)-3-hydroxypropyl]-4-oxoazetidin-2-yl]benzylcarbamoyl}ethoxy]ethoxy}-ethoxy)ethoxy]ethoxy}ethoxy)ethoxy]propionylamino}phenyl)-4-hydroxy-1,1-dioxo-2,3,4,5-tetrahydro-1H-benzo[b]thiepin-7-yl]dimethylammonium Trifluoroacetate (46)

$C_{69}H_{89}F_5N_4O_{16}S_1$ (1357.55) MS (ESI) 1243 (M+H)

EXAMPLE XXIV

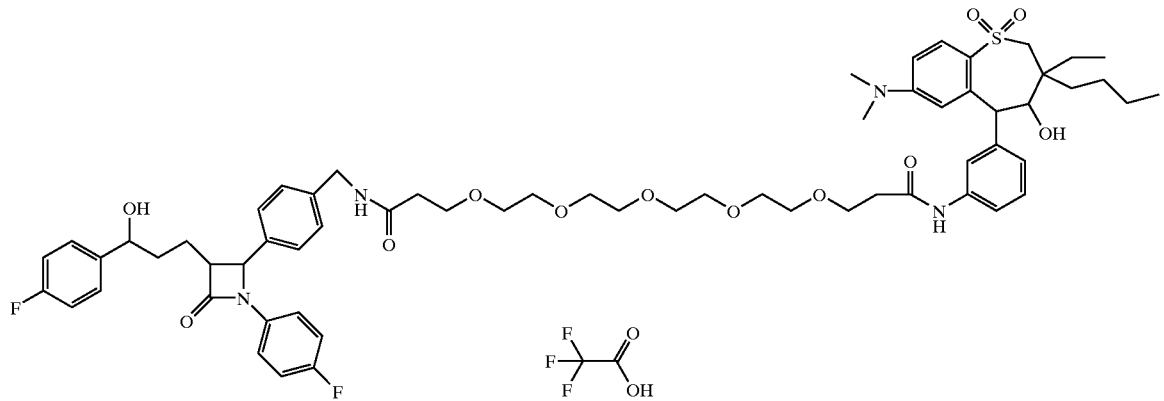

[3-Butyl-3-ethyl-5-(3-{3-[2-(2-{2-[2-({2-{2-[2-(4-{1-(4-fluorophenyl)-3-[3-(4-fluorophenyl)-3-hydroxypropyl]-4-oxoazetidin-2-yl}benzylcarbamoyl}ethoxy)ethoxy]-ethoxy}ethoxy)ethoxy]propionylamino}phenyl)-4-hydroxy-1,1-dioxo-2,3,4,5-tetrahydro-1H-benzo[b]thiepin-7-yl]dimethylammonium Trifluoroacetate (47)

$C_{65}H_{81}F_5N_4O_{14}S_1$ (1269.44) MS (ESI) 1243 (M+H).

EXAMPLE XXV

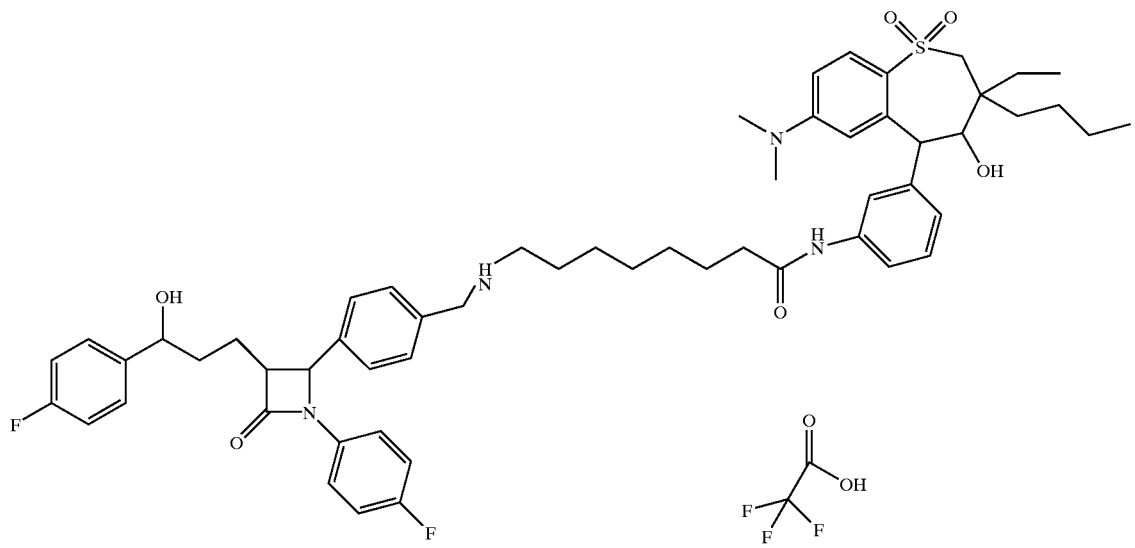

(3-Butyl-3-ethyl-5-{3-[8-(4-{(1-(4-fluorophenyl)-3-[3-(4-fluorophenyl)-3-hydroxypropyl]-4-oxoazetidin-2-yl}benzylamino)octanoylamino]phenyl}-4-hydroxy-1,1-dioxo-2,3,4,5-tetrahydro-1H-benzo[b]thiepin-7-yl)dimethylammonium Trifluoroacetate (50)

a) 7-[3-(3-Butyl-7-dimethylamino-3-ethyl-4-hydroxy-1,1-dioxo-2,3,4,5-tetrahydro-1H-benzo[b]thiepin-5-yl)-phenylcarbamoyl]heptanoic Acid (48)

The synthesis is carried out analogously to 17.

$C_{33}H_{48}N_2O_6S_1$ (600.82) MS (ESI) 601 (M+H).

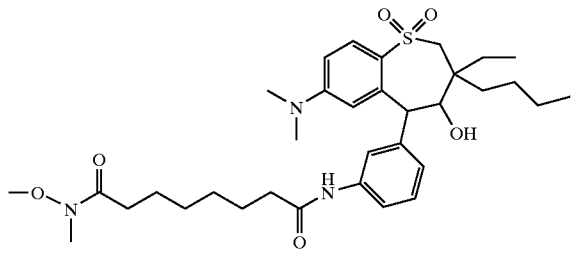

b) N-[3-(3-Butyl-7-dimethylamino-3-ethyl-4-hydroxy-1,1-dioxo-2,3,4,5-tetrahydro-1H-benzo[b]thiepin-5-yl)phenyl] N'-methoxymethyl-octanediamide (49)

At room temperature, a solution of 223 mg of O,N-dimethyl-hydroxylamine hydrochloride and 391 µl of diisopropylethylamine in 5 ml of acetonitrile is added to a solution of 550 mg of 7-[3-(3-butyl-7-dimethylamino-3-ethyl-4-hydroxy-1,1-dioxo-2,3,4,5-tetrahydro-1-benzo[b]thiepin-5-yl)phenylcarbamoyl]heptanoic acid, 311 µl of diisopropylcarbodiimide and 272 mg of hydroxybenzotriazole in 10 ml of methylene chloride, and the mixture is stirred for 12 h. The reaction solution is concentrated and purified by HPLC (Merck-Hibar-Lichrospher 100-RP-18, water (0.1% trifluoroacetic acid)/acetonitrile (0.1% trifluoroacetic acid) =80/20→10/90).

$C_{35}H_{53}N_3O_6S_1$ (643.89) MS (ESI) 644 (M+H).

c) (3-Butyl-3-ethyl-5-{3-[8-(4-{1-(4-fluorophenyl)-3-[3-(4-fluorophenyl)-3-hydroxypropyl]-4-oxoazetidin-2-yl}benzylamino)octanoylamino]phenyl}-4-hydroxy-1,1-dioxo-2,3,4,5-tetrahydro-1H-benzo[b]thiepin-7-yl) dimethylammonium Trifluoroacetate (50)

At −78° C., 0.22 ml of a 1M solution of diisobutylaluminum hydride in hexane is added to a solution of 160 mg of N-[3-(3-butyl-7-dimethylamino-3-ethyl-4-hydroxy-1,1-dioxo-2,3,4,5-tetrahydro-1H-benzo[b]thiepin-5-yl)phenyl]-N'-methoxymethyl-octane-diamide 34 in 1 ml of tetrahydrofuran, and the mixture is stirred for 30 min. Water is added to the reaction solution, and the mixture is extracted with methylene chloride. The extract is concentrated and the residue is taken up in 3 ml of a mixture of tetrahydrofuran and methanol (1/1, 1% acetic acid). 131 mg of 4-(3-aminomethylphenyl)-1-(4-fluorophenyl)-3-[3-(4-fluorophenyl)-3-hydroxypropyl]azetidin-2-one and 58 mg of sodium cyanoborohydride are added. After 12 h, water is added to the mixture, the mixture is extracted with methylene chloride and the organic phase is concentrated. The residue is purified by HPLC (Knauer Eurospher-100-10-C18, water (0.1% trifluoroacetic acid)/acetonitrile (0.1% trifluoroacetic acid)=80/20→10/90).

$C_{58}H_{72}F_2N_4O_6S_1$ (991.30) MS (ESI) 991 (M+H).

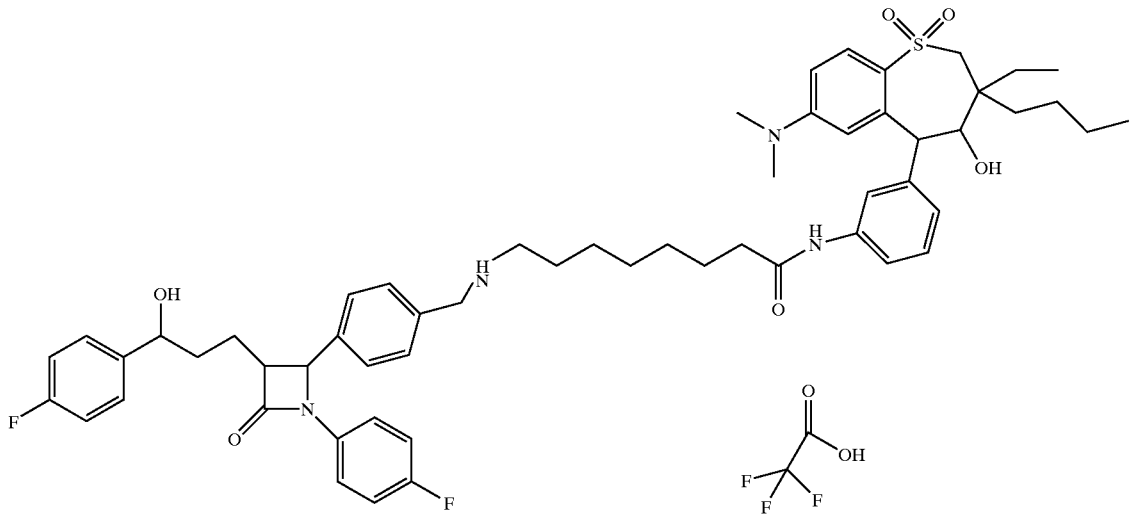

EXAMPLE XXVI

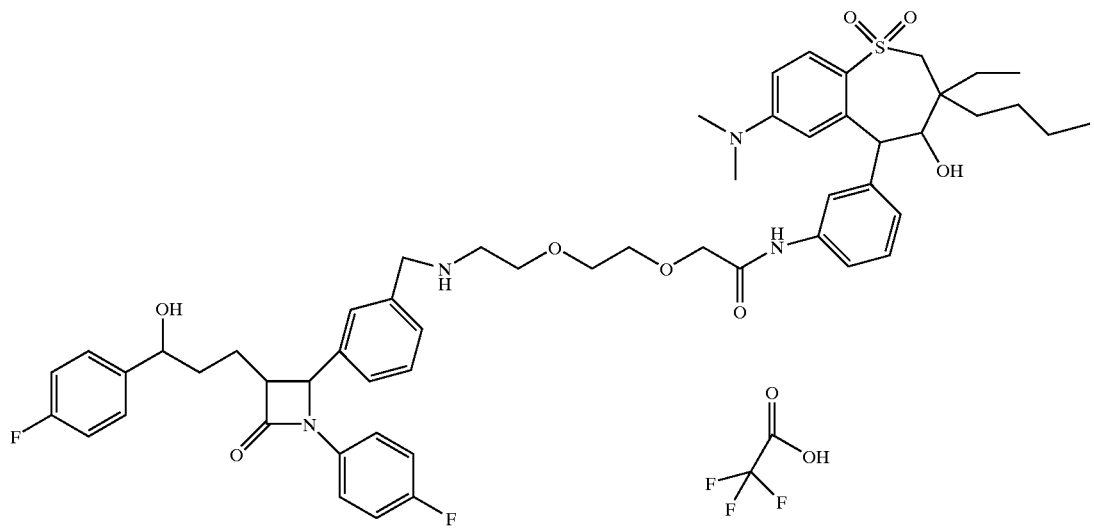

{3-Butyl-3-ethyl-5-[3-(2-{2-[2-(3-{1-(4-fluorophenyl)-3-[3-(4-fluorophenyl)-3-hydroxypropyl]-4-oxoazetidin-2-yl}benzylamino)ethoxy]ethoxy}acetylamino)phenyl]-4-hydroxy-1,1-dioxo-2,3,4,5-tetrahydro-1H-benzo[b]thiepin-7-yl}dimethylammonium Trifluoroacetate (52)

a) 2-(2-{[3-(3-Butyl-7-dimethylamino-3-ethyl-4-hydroxy-1,1-dioxo-2,3,4,5-tetrahydro-1H-benzo[b]thiepin-5-yl)phenylcarbamoyl]methoxy}ethoxy)-N-methoxy-N-methylacetamide (51)

Synthesis analogously to 49, starting from 17.
$C_{32}H_{47}N_3O_8S_1$ (633.81) MS (ESI) 634 (M+H).

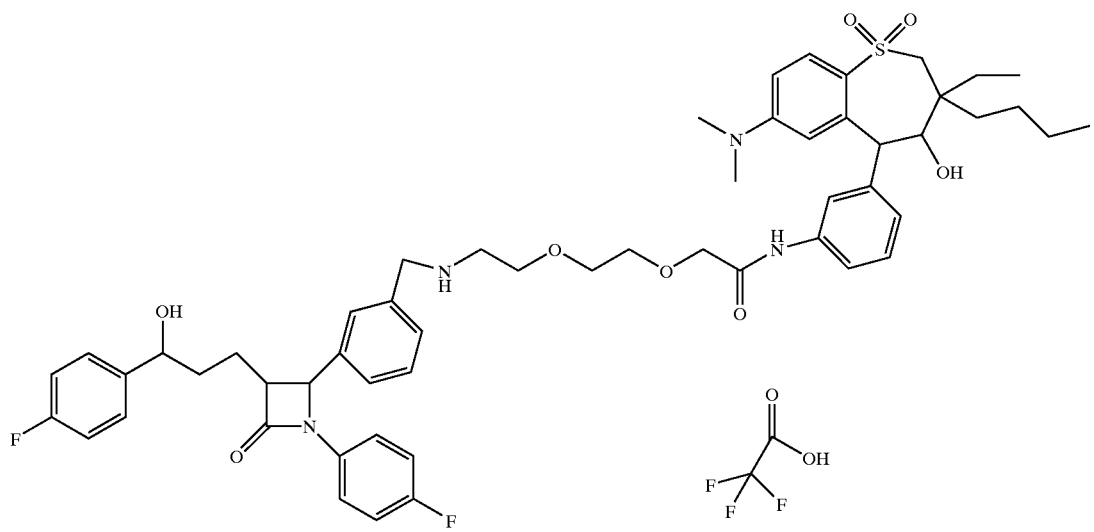

b) {3-Butyl-3-ethyl-5-[3-(2-{2-[2-(3-{1-(4-fluorophenyl)-3-[3-(4-fluorophenyl-3-hydroxypropyl]-4-oxoazetidin-2-yl}benzylamino)ethoxy]ethoxy}acetylamino)phenyl]-4-hydroxy-1,1-dioxo-2,3,4,5-tetrahydro-1H-benzo[b]thiepin-7-yl}dimethylammonium Trifluoroacetate (52)

Synthesis analogous to 50.
$C_{57}H_{67}F_5N_4O_{10}S_1$ (1095.25) MS (ESI) 982 (M+H).

EXAMPLE XXVII

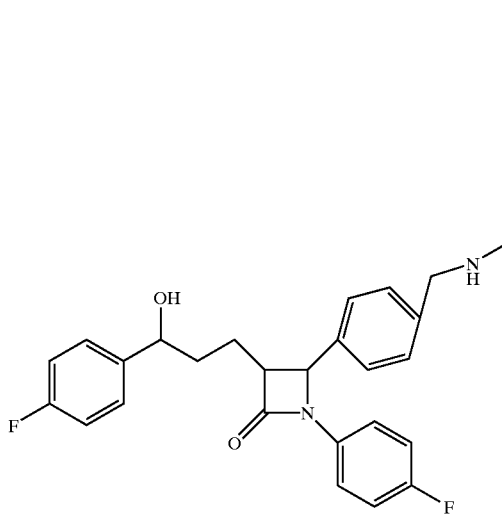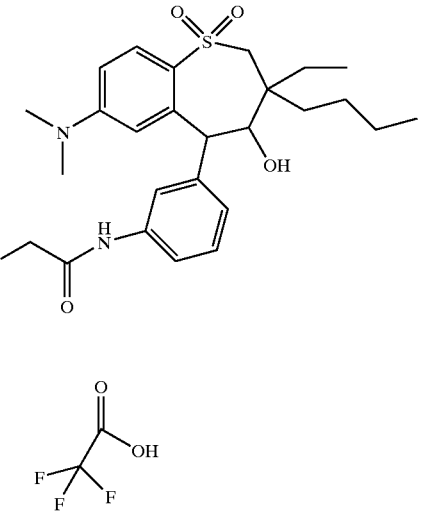

{3-Butyl-3-ethyl-5-[3-(2-{2-[2-(4-{1-(4-fluorophenyl)-3-[3-(4-fluorophenyl)-3-hydroxypropyl]-4-oxoazetidin-2-yl}benzylamino)ethoxy]ethoxy}acetylamino)phenyl]-4-hydroxy-1,1-dioxo-2,3,4,5-tetrahydro-1H-benzo[b]thiepin-7-yl}dimethylammonium Trifluoroacetate (53)

Synthesis analogous to 50.

$C_{57}H_{67}F_5N_4O_{10}S_1$ (1095.25) MS (ESI) 982 (M+H).

EXAMPLE XXVIII

A solution of 5.5 g of O,N-dimethylhydroxylamine hydrochloride and 9.6 ml of diisopropylethylamine in 50 ml of acetonitrile and 40 ml of DMF is added to a solution of 10 g of dioxaoctanedioic acid, 13 ml of diisopropylcarbodiimide and 11.4 g of hydroxybenzotriazole in 70 ml of methylene chloride, and the mixture is stirred for 12 h. The reaction solution is concentrated and purified by silica gel chromatography (ethyl acetate/heptane/methanol/acetic acid=8/10/1/1→0/0/10/1).

$C_8H_{19}N_1O_4$ (221.21) MS (ESI) 222 (M+H).

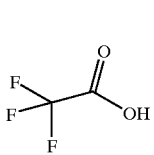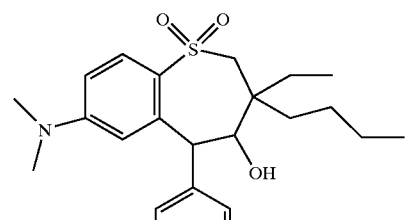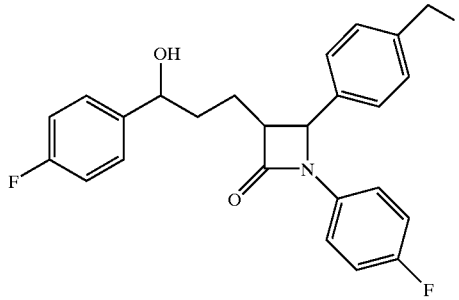

{3-Butyl-3-ethyl-5-[3-(2-{2-[(4-{1-(4-fluorophenyl)-3-[3-(4-fluorophenyl)-3-hydroxypropyl]-4-oxoazetidin-2-yl}benzylcarbamoyl)methoxy]ethoxy}ethylamino)phenyl]-4-hydroxy-1,1-dioxo-2,3,4,5-tetrahydro-1H-benzo[b]thiepin-7-yl}dimethylammonium Trifluoroacetate (58)

a) {2-[(Methoxymethylcarbamoyl)methoxy]ethoxy}acetic Acid (54)

b) tert-Butyl {2-[(Methoxymethylcarbamoyl)methoxy]ethoxy}acetate (55)

1.3 ml of thionyl chloride are added to a solution of 2 g of {2-[(methoxymethylcarbamoyl)methoxy]ethoxy}acetic acid 39 in 20 ml of methylene chloride, and the mixture is stirred at 60° C. for 1 h. 1.3 ml of tert-butanol are added, and the mixture is then stirred at room temperature for another 2 h. Water is added, the mixture is extracted with methylene chloride and the extract is concentrated, giving 55.

$C_{12}H_{23}N_1O_6$ (277.32) MS (ESI) 222 (M+2*H-tert-butyl).

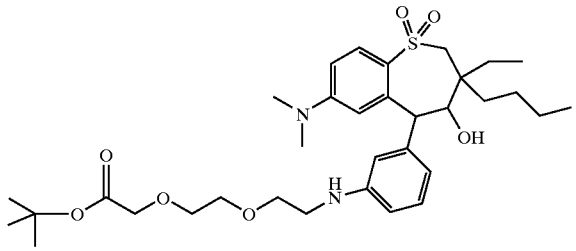

c) tert-Butyl (2-{2-[3-(3-Butyl-7-dimethylamino-3-ethyl-4-hydroxy-1,1-dioxo-2,3,4,5-tetrahydro-1H-benzo[b]thiepin-5-yl)phenylamino]ethoxy}ethoxy)acetate (56)

Synthesis analogous to 50 starting from 55 and 5-(3-aminophenyl)-3-butyl-7-dimethylamino-3-ethyl-1,1-dioxo-2,3,4,5-tetrahydro-1H-benzo[b]thiepin-4-ol.

d) (3-Butyl-5-{3-[2-(2-carboxymethoxyethoxy)ethylamino]phenyl}-3-ethyl-4-hydroxy-1,1-dioxo-2,3,4,5-tetrahydro-1H-benzo[b]thiepin-7-yl)dimethylammonium Trifluoroacetate (57)

A solution of 90 mg of tert-butyl (2-{2-[3-(3-butyl-7-dimethylamino-3-ethyl-4-hydroxy-1,1-dioxo-2,3,4,5-tetrahydro-1H-benzo[b]thiepin-5-yl)phenylamino]ethoxy}ethoxy)acetate in 1 ml of methylene chloride and 1 ml of trifluoroacetic acid is stirred for 2 h and then concentrated. The product is purified by HPLC (Knauer Eurospher-100-10-C18, water (0.1% trifluoroacetic acid)/acetonitrile (0.1% trifluoroacetic acid)=80/20→10/90).

$C_{30}H_{44}N_2O_7S_1$ (576.76) MS (ESI) 577 (M+H).

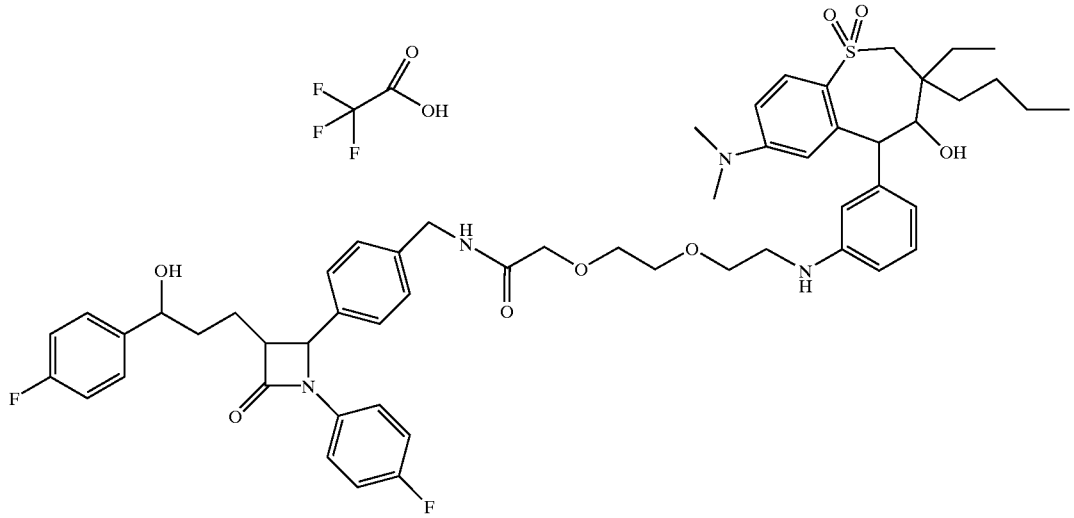

$C_{34}H_{52}N_2O_7S_1$ (632.87) MS (ESI) 577 (M+2*H-tert-Bu)

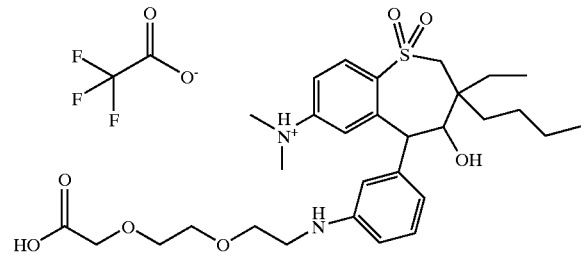

e) {3-Butyl-3-ethyl-5-[3-(2-{2-[(4-{1-(4-fluorophenyl)-3-[3-(4-fluorophenyl)-3-hydroxypropyl]-4-oxoazetidin-2-yl}benzylcarbamoyl)methoxy]ethoxy}ethylamino)phenyl]-4-hydroxy-1,1-dioxo-2,3,4,5-tetrahydro-1H-benzo[b]thiepin-7-yl}dimethylammonium Trifluoroacetate (58)

55 mg of 4-(4-aminomethylphenyl)-1-(4-fluorophenyl)-3-[3-(4-fluorophenyl)-3-hydroxypropyl]azetidin-2-one are added to a solution of 40 mg of (2-{2-[3-(3-butyl-7-dimethylamino-3-ethyl-4-hydroxy-1,1-dioxo-2,3,4,5-tetrahydro-1H-benzo[b]thiepin-5-yl)phenylamino]ethoxy}ethoxy)acetic acid compound with trifluoroacetic acid, 37 µl of diisopropylcarbodiimide, 26 mg of hydroxybenzotriazole and 40 µl of triethylamine in 2 ml of dimethylformamide, and the mixture is stirred for 12 h. The reaction solution is concentrated and separated by HPLC (Merck-Hibar-Lichrospher 100-RP-18, water (0.1% trifluoroacetic acid)/acetonitrile (0.1% trifluoroacetic acid)=80/20→10/90).

$C_{57}H_{67}F_5N_4O_{10}S_1$ (1095.22) MS (ESI) 981 (M+H).

EXAMPLE XXIX

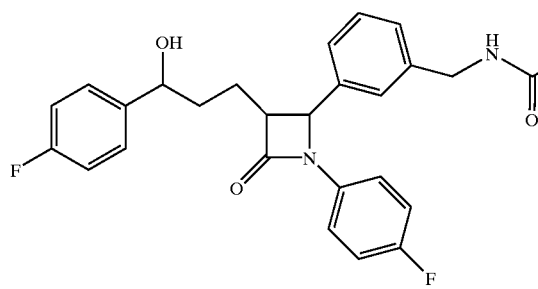
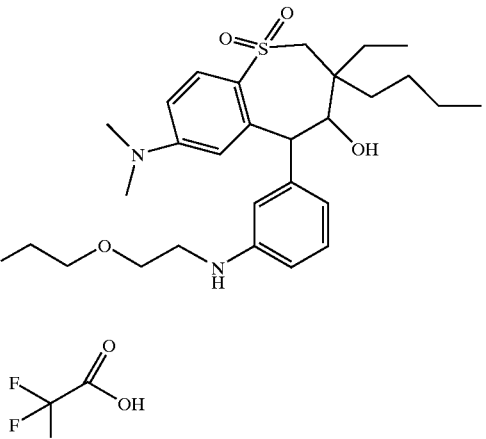

{3-Butyl-3-ethyl-5-[3-(2-{2-[(3-{1-(4-fluorophenyl)-3-[3-(4-fluorophenyl)-3-hydroxypropyl]-4-oxoazetidin-2-yl}benzylcarbamoyl)methoxy]ethoxy}ethylamino)phenyl]-4-hydroxy-1,1-dioxo-2,3,4,5-tetrahydro-1H-benzo[b]thiepin-7-yl}dimethylammonium Trifluoroacetate (59)

Synthesis analogous to 58.

$C_{57}H_{67}F_5N_4O_{10}S_1$ (1095.22) MS (ESI) 981 (M+H).

EXAMPLE XXX

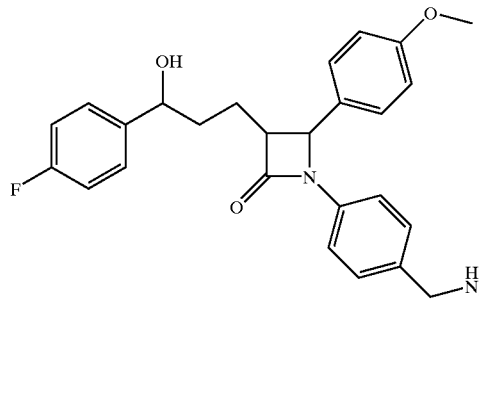
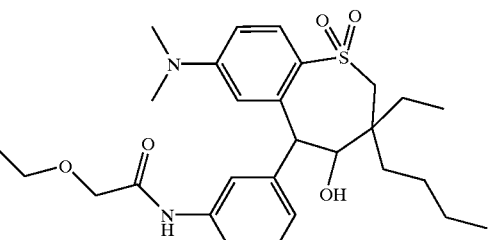

2-(2-{[3-(3-Butyl-7-dimethylamino-3-ethyl-4-hydroxy-1,1-dioxo-2,3,4,5-tetrahydro-1H-benzo[b]thiepin-5-yl)phenylcarbamoyl]methoxy}ethoxy)-N-{4-[3-[3-(4-fluorophenyl)-3-hydroxypropyl]-2-(4-methoxyphenyl)-4-oxoazetidin-1-yl]benzyl}acetamide (65)

a) 3-[5-(tert-Butyldimethylsilanyloxy)-5-(4-fluorophenyl)pentanoyl]-4-phenyloxazolidin-2-one (60)

27 g of 3-[5-(4-fluorophenyl)-5-hydroxypentanoyl]-4-phenyloxazolidin-2-one, 13.6 g of tert-butyldimethylsilyl chloride and 10,2 g of imidazole are dissolved in 36 ml of dimethylformamide and stirred at 60° C. for 90 min. After the end of the reaction, the mixture is dissolved in ethyl acetate and extracted twice with water. The organic phase is dried over magnesium sulfate, filtered and concentrated under reduced pressure. This gives 3-[5-(tert-butyldimethylsilanyloxy)-5-(4-fluorophenyl)pentanoyl]-4-phenyloxazolidin-2-one of molecular weight 471.65 ($C_{26}H_{34}FNO_4Si$); MS (ESI): 340.28 (MH$^+$–HOSi(CH$_3$)$_2$C(CH$_3$)$_3$)

b) 4-[5-(tert-Butyldimethylsilanyloxy)-5-(4-fluorophenyl)-1-(4-methoxyphenyl)-2-(2-oxo-4-phenyloxazolidine-3-carbonyl)pentylamino]benzonitrile (61)

16.2 g of 3-[5-(tert-butyldimethylsilanyloxy)-5-(4-fluorophenyl)pentanoyl]-4-phenyloxazolidin-2-one are dissolved in 350 ml of dichloromethane. 19.8 ml of Hünig base and 10.14 g of 4-[(4-methoxyphenylimino)methyl]benzonitrile are added to the solution, and the solution is cooled to −10° C. 8.52 ml of trimethylsilyl triflate are added to the cooled solution, and the solution is stirred at −10° C. for 30 min. The solution is then cooled to −30° C., and 44 ml of titanium tetrachloride solution are added. The reaction mixture is stirred at from −30 to −40° C. for 2 h. The solution is then allowed to warm to room temperature and washed successively with 200 ml of 2N sulfuric acid, 300 ml of 20% strength sodium hydrogen sulfite solution and sat. sodium chloride solution. The organic phase is dried over magnesium sulfate and concentrated under reduced pressure and the residue is purified on silica gel using n-heptane/ethyl acetate 3/1. This gives 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitrile of molecular weight 707.93 ($C_{41}H_{46}FN_3O_5Si$); MS (ESI): 590.51 (MH$^+$–$C_7H_5N_2$).

c) 4-[3-[3-(tert-Butyldimethylsilanyloxy)-3-(4-fluorophenyl)propyl]-2-(4-methoxyphenyl)-4-oxoazetidin-1-yl]benzonitrile (62)

13.2 g of 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitrile are dissolved in 380 ml of methyl tert-butyl ether, 18.6 ml of N,O-bis(trimethylsilyl)acetamide and 1.86 ml of a 1 M solution of tetrabutylammonium fluoride in tetrahydrofuran are added and the mixture is stirred at room temperature for 2 h. Once the reaction has ended, 10 ml of acetic acid are added, the reaction mixture is concentrated under reduced pressure and the residue is purified on silica gel using toluene/ethyl acetate 50/1. This gives 4-[3-[3-(tert-butyldimethylsilanyloxy)-3-(4-fluorophenyl)propyl]-2-(4-methoxyphenyl)-4-oxoazetidin-1-yl]benzonitrile of molecular weight 544.75 ($C_{32}H_{37}FN_2O_3Si$); MS (ESI): 545.56 ($M+H^+$).

d) 4-[3-[3-(4-Fluorophenyl)-3-hydroxypropyl]-2-(4-methoxyphenyl)-4-oxoazetidin-1-yl]benzonitrile (63)

3.5 g of 4-[3-[3-(tert-butyldimethylsilanyloxy)-3-(4-fluorophenyl)propyl]-2-(4-methoxyphenyl)-4-oxoazetidin-1-yl]benzonitrile are dissolved in 65 ml of tetrahydrofuran, 0.74 ml of acetic acid and 8.03 ml of a 1 M solution of tetrabutylammonium fluoride in tetrahydrofuran are added and the mixture is stirred at room temperature for 2 h. Another 4.82 ml of the tetrabutylammonium fluoride solution are then added, and stirring is continued at reflux temperature for another 3 h. The cooled reaction mixture is concentrated under reduced pressure and the residue is purified by silica gel chromatography using n-heptane/ethyl acetate 2/1. This gives 4-[3-[3-(4-fluorophenyl)-3-hydroxypropyl]-2-(4-methoxyphenyl)-4-oxoazetidin-1-yl]benzonitrile of molecular weight 430.48 ($C_{26}H_{23}FN_2O_3$); MS (ESI): 431.24 ($M+H^+$).

e) 1-(4-Aminomethylphenyl)-3-[3-(4-fluorophenyl)-3-hydroxypropyl]-4-(4-methoxy-phenyl)azetidin-2-one (64)

1.22 g of 4-[3-[3-(4-fluorophenyl)-3-hydroxypropyl]-2-(4-methoxyphenyl)-4-oxoazetidin-1-yl]benzonitrile are dissolved in 90 ml of ethanol, 10 ml of conc. ammonia solution and an excess of Raney nickel are added and the mixture is stirred at 60° C. and a hydrogen pressure of 10 bar for 8 h. The reaction mixture is allowed to cool to room temperature overnight; the next day, the catalyst is removed, the filtrate is concentrated under reduced pressure and the residue is purified by silica gel gives 1-(4-aminomethylphenyl)-3-[3-(4-fluorophenyl)-3-hydroxypropyl]-4-(4-methoxyphenyl)azetidin-2-one of molecular weight 434.51 ($C_{26}H_{27}FN_2O_3$); MS (ESI): 418.2 ($MH^+$–$NH_3$).

f) 2-(2-{[3-(3-Butyl-7-dimethylamino-3-ethyl-4-hydroxy-1,1-dioxo-2,3,4,5-tetrahydro-1H-benzo[b]thiepin-5-yl)phenylcarbamoyl]methoxy}ethoxy)-N-{4-[3-[3-(4-fluorophenyl)-3-hydroxypropyl]-2-(4-methoxyphenyl)-4-oxoazetidin-1-yl]benzyl}acetamide (65)

At room temperature, 140 mg of (2-{[3-(3-butyl-7-dimethylamino-3-ethyl-4-hydroxy-1,1-dioxo-2,3,4,5-tetrahydro-1H-benzo[b]thiepin-5-yl)-phenylcarbamoyl]methoxy}-ethoxy)acetic acid (17) and 100 mg of 1-(4-aminomethylphenyl)-3-[3-(4-fluorophenyl)-3-hydroxypropyl]-4-(4-methoxyphenyl)azetidin-2-one are dissolved in 5 ml of dimethylformamide, 35 mg of 1-hydroxybenzotriazole and 45 mg of 1-ethyl-3-(3-dimethylaminopropyl)carbodiimide hydrochloride are added and the mixture is stirred at room temperature for 6 h. The reaction mixture is concentrated under reduced pressure. Dichloromethane is added to the residue, the mixture is extracted twice with water and once with sat. sodium chloride solution and the organic extract is dried over magnesium sulfate, filtered and concentrated under reduced pressure. The crude product is purified chromatographically (RP18; dichloromethane/methanol 92/8, changed over 25 min to dichloromethane/methanol 96/4). This gives the product of melting point 116–125° C. Molecular weight 1007.24 ($C_{56}H_{67}FN_4O_{10}S$); MS (ESI): 1008.53 ($M+H^+$).

EXAMPLE XXXI

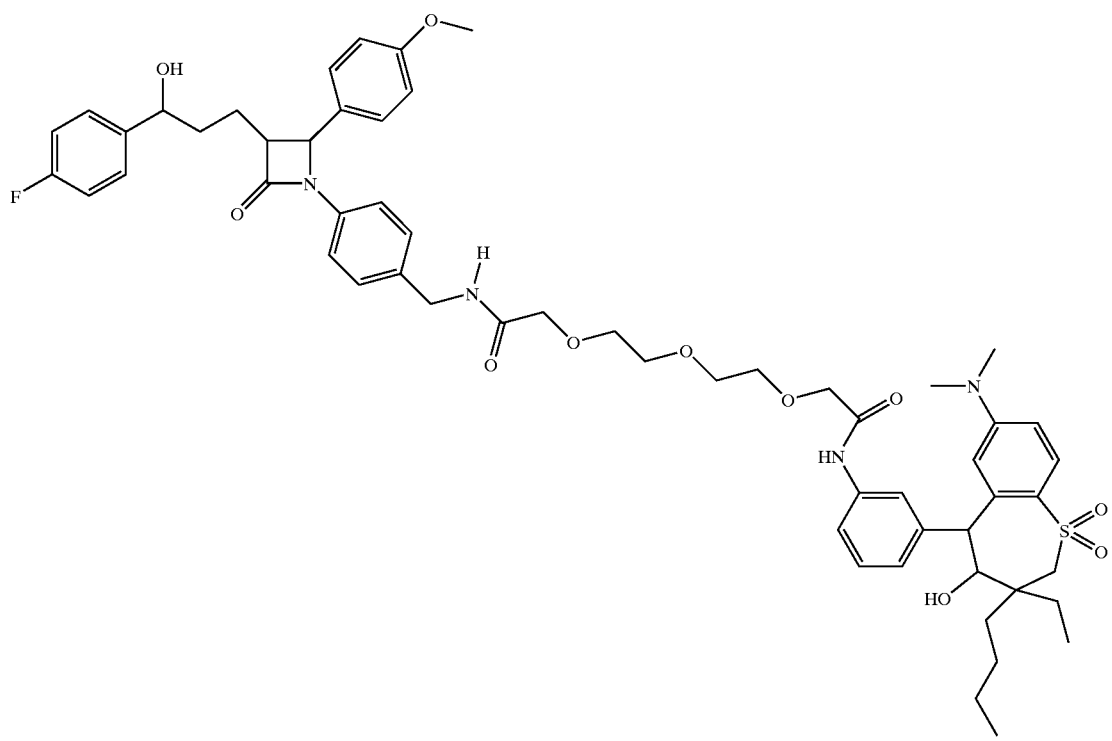

N-[3-(3-Butyl-7-dimethylamino-3-ethyl-4-hydroxy-1,1-dioxo-2,3,4,5-tetrahydro-1H-benzo[b]thiepin-5-yl)phenyl]-2-{2-[2-({4-[3-[3-(4-fluorophenyl)-3-hydroxypropyl]-2-(4-methoxyphenyl)-4-oxoazetidin-1-yl]benzylcarbamoyl}methoxy)ethoxy]ethoxy}acetamide (66)

The compound of example 3 is prepared like that of example 2, with the difference, that [2-(2-{[3-(3-butyl-7-dimethylamino-3-ethyl-4-hydroxy-1,1-dioxo-2,3,4,5-tetrahydro-1H-benzo[b]thiepin-5-yl)phenylcarbamoyl]methoxy}ethoxy)ethoxy]acetic acid (20) is used instead of (17).

Molecular weight 1051.29 ($C_{58}H_{71}FN_4O_{11}S$); MS (ESI): 1052.51 ($M+H^+$).

Using the method described below, the activity of the compounds of the formula I according to the invention was examined:

Effect on Cholesterol Absorption +$^3$H-taurocholic Acid Excretion Using Fecal Excrement of Mice, Rats or Hamsters NMRI mice, Wistar rats, or Golden Syrian hamsters (in groups of n=4–6) are kept in metabolic cages, where they are fed with a standard diet (Altromin, Lage (Lippe)). The afternoon prior to the administration of the radioactive tracers ($^{14}$C-cholesterol), the feed is removed and the animals are adapted to grates.

Additionally, the animals are labeled s.c. with $^3$H-TCA (taurocholic acid) (for example 1 µCi/mouse up to 5 µCi/rat) 24 hours prior to the peroral administration of the test meal ($^{14}$C-cholesterol in Intralipid® 20, Pharmacia-Upjohn).

Cholesterol absorption test: 0.25 ml/mouse Intralipid ® 20 (Pharmacia-Upjohn) ((Spiked with 0.25 µCi of $^{14}$C-cholesterol in 0.1 mg of cholesterol) are administered per-orally by gavage.

Test substances were prepared separately in 0.5% methylcellulose (Sigma)/5% Solutol (BASF, Ludwigshafen) or a suitable vehicle.

The administration volume of the test substance is 0.5 ml/mouse. The test substance is administered immediately prior to the test meal (Intralipid labeled with $^{14}$C-cholesterol) (cholesterol absorption test).

The feces are collected over a period of 24 h: fecal elimination of $^{14}$C-cholesterol and $^3$H-taurocholic acid (TCA) is determined after 24 hours.

The livers are removed and homogenized, and aliquots are incinerated in an oximate (Model 307, Packard) to determine the amount of $^{14}$C-cholesterol which had been taken up/absorbed.

Evaluation

Feces Samples:

The total weight is determined, the sample is made up with water to a defined volume and then homogenized, and an aliquot is evaporated to dryness and incinerated in an oximate (Model 307 from Packard for the incineration of radioactively labeled samples): the amount of radioactive $^3$H—$H_2O$ and $^4$C—$CO_2$ is extrapolated to the amount of $^3$H-taurocholic acid and $^{14}$C-cholesterol, respectively, that is excreted (dual isotope technique). The $ED_{200}$ values as dose from a dose effect curve are interpolated as those doses at which the excretion of TCA or cholesterol is doubled, based on a control group treated at the same time.

Liver Samples

The amount of $^{14}$C-cholesterol taken up by the liver is based on the administered dose. The $ED_{50}$ values are interpolated from a dose-effect curve as the dose at of which the uptake of $^{14}$C-cholesterol by the liver is halved (50%), based on a control group.

The $ED_{50}$ values below demonstrate the activity of the compounds of the formula I according to the invention

| Example No. | $ED_{50}$ (liver) [mg/mouse] |
|---|---|
| II | 0.01 |
| III | 0.03 |
| VIII | 0.003 |
| XXV | 0.01 |
| XXXI | 0.1 |

As can be seen from the table, the compounds of the formula I have very good cholesterol-lowering action. The compounds can thus be used to control cholesterol concentration. Such control can be by lowering the cholesterol concentration, or maintaining a desired level of cholesterol concentration.

Bioabsorption

The bioabsorption of the compounds of the formula I was examined using the Caco cell model (A. R. Hilgers et al., Caco-2 cell monolayers as a model for drug transport across the intestinal mucosa, Pharm. Res. 1990, 7, 902).

From the measured data, it can be seen that the bioabsorption of the compounds of the formula I according to the invention is considerably lower than that of compounds described in the prior art (reference structure):

| | Reference structure | Example XII |
|---|---|---|
| Apparent partition coefficient $P_{app}$ [cm/s] (according to Lit. Hilgers) | $4.88 \times 10^{-06}$ | $3.67 \times 10^{-09}$ |
| Estimated human bioabsorption | 100% | <1% |

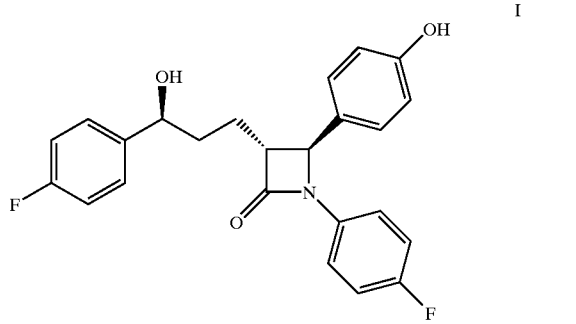

Reference structure: Ezetimibe

We claim:
1. A compound of the formula I,

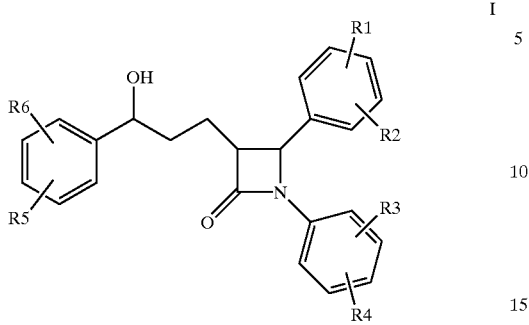

or a pharmaceutically acceptable salt or ester thereof, in which

R1, R2, R3, R4, R5, R6 independently of one another are $(C_0-C_{30})$-alkylene-L, where one or more carbon atoms of the alkylene radical may be replaced by —O—, —(C=O)—, —CH=CH—, —C≡C—, —N(($C_1-C_6$)-alkyl)- or —NH—; or H, F, Cl, Br, I, $CF_3$, $NO_2$, CN, COOH, COO($C_1-C_6$)-alkyl, $CONH_2$, CONH($C_1-C_6$)-alkyl, CON[($C_1-C_6$)-alkyl]$_2$, ($C_1-C_6$)-alkyl, ($C_2-C_6$)-alkenyl, ($C_2-C_6$)-alkynyl or O—($C_1-C_6$)-alkyl, where one or more hydrogens in the alkylene radicals may be replaced by fluorine; or $SO_2$—$NH_2$, $SO_2$NH($C_1-C_6$)-alkyl, $SO_2$N[($C_1-C_6$)-alkyl]$_2$, S—($C_1-C_6$)-alkyl, S—($CH_2$)$_n$-phenyl, SO—($C_1-C_6$)-alkyl, SO—($CH_2$)$_n$-phenyl, $SO_2$—($_1-C_6$)-alkyl or $SO_2$—($CH_2$)$_n$-phenyl, where n=0–6 and the phenyl radical may be substituted up to two times by F, Cl, Br, OH, $CF_3$, $NO_2$, CN, $OCF_3$, O—($C_1-C_6$)-alkyl, ($C_1-C_6$)-alkyl or $NH_2$; or $NH_2$, NH—($C_1-C_6$)-alkyl, N(($C_1-C_6$)-alkyl)$_2$, NH($C_1-C_7$)-acyl, phenyl or O—($CH_2$)$_n$-phenyl, where n=0–6, where the phenyl ring may be mono- to trisubstituted by F, Cl, Br, I, OH, $CF_3$, $NO_2$, CN, $OCF_3$, O—($C_1-C_6$)-alkyl, ($C_1-C_6$)-alkyl, $NH_2$, NH($C_1-C_6$)-alkyl, N(($C_1-C_6$)-alkyl)$_2$, $SO_2$—$CH_3$, COOH, COO—($C_1-C_6$)-alkyl or $CONH_2$;

is shown connected to $(C_0-C_{30})$-alkylene as follows:

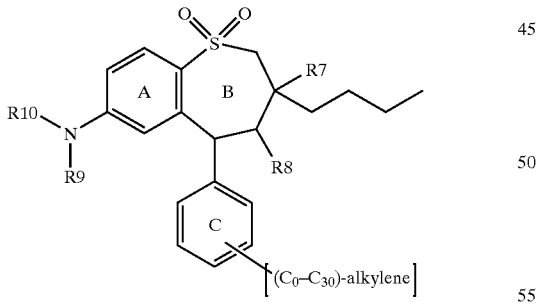

R7 is methyl, ethyl, propyl or butyl;
R8 is H, OH, $NH_2$ or NH—($C_1-C_6$)-alkyl;
R9 is methyl, ethyl, propyl or butyl;
R10 is methyl, ethyl, propyl or butyl;
wherein at least one of the radicals R1 to R6 has the meaning $(C_0-C_{30})$-alkylene-L, where one or more carbon atoms of the alkylene radical may be replaced by —O—, —(C=O)—, —CH=CH—, —C≡C—, —N(($C_1-C_6$)-alkyl)- or —NH—.

2. A compound as claimed in claim 1, wherein
R1, R2, R3, R4, R5, R6 independently of one another are $(C_0-C_{30})$-alkylene-L, where one or more carbon atoms of the alkylene radical may be replaced by —O—, —(C=O)- or —NH—; or H, F, Cl, Br, I, $CF_3$, $NO_2$, CN, COOH, COO($C_1-C_6$)-alkyl, $CONH_2$, CONH($C_1-C_6$)alkyl, CON[($C_1-C_6$)alkyl]$_2$, ($C_1-C_6$)-alkyl, ($C_2-C_6$)-alkenyl, ($C_2-C_6$)-alkynyl or O—($C_1-C_6$)-alkyl, where one or more hydrogens in the alkylene radicals may be replaced by fluorine; or $SO_2$—$NH_2$, $SO_2$NH($C_1-C_6$)-alkyl, $SO_2$N[($C_1-C_6$)-alkyl]$_2$, S—($C_1-C_6$)-alkyl, S—($CH_2$)$_n$-phenyl, SO—($C_1-C_6$)-alkyl, SO—($CH_2$)$_n$-phenyl, $SO_2$—($C_1-C_6$)-alkyl or $SO_2$—($H_2$)$_n$-phenyl, where n=0–6 and the phenyl radical may be substituted up to two times by F, Cl, Br, OH, $CF_3$, $NO_2$, CN, $OCF_3$, O—($C_1-C_6$)-alkyl, ($C_1-C_6$)-alkyl or $NH_2$; or $NH_2$, NH—($C_1-C_6$)-alkyl, N(($C_1-C_6$)-alkyl)$_2$, NH($C_1-C_7$)-acyl, phenyl or O—($CH_2$)$_n$-phenyl, where n=0–6, where the phenyl ring may be mono- to trisubstituted by F, Cl, Br, I, OH, $CF_3$, $NO_2$, CN, $OCF_3$, O—($C_1-C_6$)-alkyl, ($C_1-C_6$)-alkyl, $NH_2$, NH($C_1-C_6$)-alkyl, N(($C_1-C_6$)-alkyl)$_2$, $SO_2$—$CH_3$, COOH, COO—($C_1-C_6$)-alkyl or $CONH_2$;

is shown connected to $(C_0-C_{30})$-alkylene as follows:

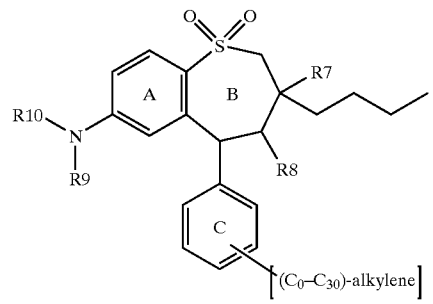

R7 is methyl, ethyl, propyl or butyl;
R8 is H, OH, $NH_2$ or NH—($C_1-C_6$)-alkyl;
R9 is methyl, ethyl, propyl or butyl;
R10 is methyl, ethyl, propyl or butyl;
wherein at least one of the radicals R1 to R6 has the meaning $(C_0-C_{30})$-alkylene-L, where one or more carbon atoms of the alkylene radical may be replaced by —O—, —(C=O)- or —NH—.

3. A compound as claimed in claim 1, wherein
R1, R2, R3, R4, R5, R6 independently of one another are $(C_0-C_{30})$-alkylene-L, where one or more carbon atoms of the alkylene radical may be replaced by —O—, —(C=O)- or —NH—; or H, F, Cl, Br, I, $CF_3$, $NO_2$, CN, COOH, COO($C_1-C_6$)-alkyl, $CONH_2$, CONH($C_1-C_6$)-alkyl, CON[($C_1-C_6$)-alkyl]$_2$, ($C_1-C_6$)-alkyl, ($C_2-C_6$)-alkenyl, ($C_2-C_6$)-alkynyl or O—($C_1-C_6$)-alkyl, where one or more hydrogens in the alkylene radicals may be replaced by fluorine; or $SO_2$—$NH_2$, $SO_2$NH($C_1-C_6$)-alkyl, $SO_2$N[($C_1-C_6$)-alkyl]$_2$, S—($C_1-C_6$)-alkyl, S—($CH_2$)$_n$-phenyl, SO—($C_1-C_6$)-alkyl, SO—($CH_2$)$_n$-phenyl, $SO_2$—($_1-C_6$)-alkyl or $SO_2$—($H_2$)$_n$-phenyl, where n=0–6 and the phenyl radical may be substituted up to two times by F, Cl, Br, OH, $CF_3$, $NO_2$, CN, $OCF_3$, O—($C_1-C_6$)-alkyl, ($C_1-C_6$)-alkyl or $NH_2$; or $NH_2$, NH—($C_1-C_6$)-alkyl, N(($C_1-C_6$)-alkyl)$_2$, NH($C_1-C_7$)-acyl, phenyl or O—($CH_2$)$_n$-phenyl, where n=0–6, where the phenyl ring may be mono- to trisubstituted by F, Cl, Br, I, OH, $CF_3$, $NO_2$, CN, $OCF_3$, O—($C_1-C_6$)-alkyl, ($C_1-C_6$)-alkyl, $NH_2$, NH($C_1-C_6$)-alkyl, N(($C_1-C_6$)-alkyl)$_2$, $SO_2$—$CH_3$, COOH, COO—($C_1-C_6$)-alkyl or $CONH_2$;

is shown connected to $(C_0-C_{30})$-alkylene as follows:

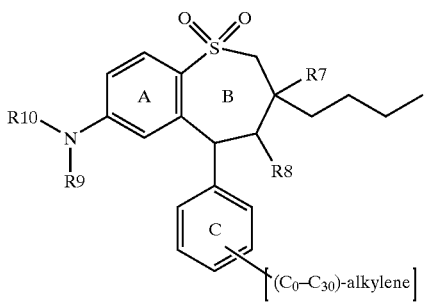

R7 is methyl, ethyl, propyl or butyl;
R8 is H, OH, $NH_2$ or $NH-(C_1-C_6)$-alkyl;
R9 is methyl, ethyl, propyl or butyl;
R10 is methyl, ethyl, propyl or butyl;
where one of the radicals R1 or R3 has the meaning $(C_0-C_{30})$-alkylene-L, where one or more carbon atoms of the alkylene radical may be replaced by —O—, —(C=O)- or —NH—.

4. A compound as claimed in claim 1, wherein
R1, R2, R3, R4, R5, R6 independently of one another are
—$(CH_2)_{0-1}$—NH—$(C=O)_{0-1}$—$(C_3-C_{25})$-alkylene-$(C=O)_{0-1}$—NH—L, where one or more carbon atoms of the alkylene radical may be replaced by oxygen atoms; or
H, F, Cl, Br, I, $CF_3$, $NO_2$, CN, COOH, COO($C_1-C_6$)-alkyl, $CONH_2$, CONH($C_1-C_6$)-alkyl, CON[($C_1-C_6$)-alkyl]$_2$, ($C_1-C_6$)-alkyl, ($C_2-C_6$)-alkenyl, ($C_2-C_6$)-alkynyl or O—($C_1-C_6$)-alkyl, where one or more hydrogens in the alkylene radicals may be replaced by fluorine; or
$SO_2$—$NH_2$, $SO_2NH(C_1-C_6)$-alkyl, $SO_2N[(C_1-C_6)$-alkyl]$_2$, S—($C_1-C_6$)-alkyl, S—$(CH_2)_n$-phenyl, SO—($C_1-C_6$)-alkyl, SO—$(CH_2)_n$-phenyl, $SO_2$—($C_1-C_6$)-alkyl or $SO_2$—$(H_2)_n$-phenyl, where n=0–6 and the phenyl radical may be substituted up to two times by F, Cl, Br, OH, $CF_3$, $NO_2$, CN, $OCF_3$,
O—($C_1-C_6$)-alkyl, ($C_1-C_6$)-alkyl or $NH_2$; or $NH_2$, NH—($C_1-C_6$)-alkyl, N(($C_1-C_6$)-alkyl)$_2$, NH($C_1-C_7$)-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—($C_1-C_6$)-alkyl, ($C_1-C_6$)-alkyl, $NH_2$, NH($C_1-C_6$)-alkyl, N(($C_1-C_6$)-alkyl)$_2$, $SO_2$—$CH_3$, COOH, COO—($C_1-C_6$)-alkyl or $CONH_2$;
is shown connected to $(C_0-C_{30})$-alkylene as follows:

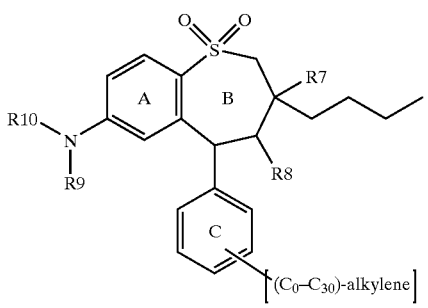

R7 is methyl, ethyl, propyl or butyl;
R8 is H, OH, $NH_2$ or $NH-(C_1-C_6)$-alkyl;
R9 is methyl, ethyl, propyl or butyl;
R10 is methyl, ethyl, propyl or butyl;
where one of the radicals R1 to R3 has the meaning —$(CH_2)_{0-1}$—NH—$(C=O)_{0-1}$—$(C_3-C_{25})$-alkylene-$(C=O)_{0-1}$—NH—L, where one or more carbon atoms of the alkylene radical may be replaced by oxygen atoms.

5. A pharmaceutical composition comprising one or more of the compounds as claimed in claim 1 and a pharmaceutically acceptable carrier.

6. A pharmaceutical composition comprising one or more compounds as claimed claim 1 and at least one further active compound.

7. A pharmaceutical composition as claimed in claim 6, comprising, as a further active compound, one or more compounds that normalize lipid metabolism.

8. A pharmaceutical composition as claimed in claim 6, comprising, as a further active compound, one or more antidiabetics, hypoglycemically active compounds, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyases inhibitors, squalene synthetase inhibitors, lipoprotein(a) antagonists, lipase inhibitors, insulins, sulphonyl ureas, biguanides, meglitinides, thiolidindiones, α-glucosidase inhibitors, active compounds which act on the ATP-dependent potassium channel of the beta cells, CART agonists, NPY agonists, MC4 agonists, orexin agonists, H3 agonists, TNF agonists, CRF agonists, CRF BP agonists, urocortin agonists, β3 agonists, MSH (melanocyte-stimulating hormone) agonists, CCK agonists, serotonin-reuptake inhibitors, mixed serotonin and noradrenergic compounds, 5HT agonists, bombesin agonists, galanin agonists, growth hormones, growth hormone-releasing compounds, TRH agonists, decoupling protein 2- or 3-modulators, leptin agonists, DA agonists, lipase/amylase inhibitors, PPAR modulators, RxR modulators or TR-β-agonists or amphetamines.

9. A method for controlling the serum cholesterol concentration in a host, which comprises administering to the host in need of the control of serum cholesterol concentration an effective amount of at least one compound as claimed in claim 1.

10. A method for the treatment of at least one disorder selected from impaired lipid metabolism, hyperlipidemia, an arteriosclerotic symptom, and insulin resistance, which comprises administering to a host in need of the treatment an effective amount of at least one compound as claimed in claim 1.

11. A method as claimed in claim 10, wherein the host suffers from impaired lipid metabolism.

12. A method as claimed in claim 10, wherein the host suffers from hyperlipidemia.

13. A method as claimed in claim 10, wherein the host suffers from an arteriosclerotic symptom.

14. A method as claimed in claim 10, wherein the host suffers from insulin resistance.

* * * * *

UNITED STATES PATENT AND TRADEMARK OFFICE
CERTIFICATE OF CORRECTION

PATENT NO.    : 6,498,156 B2
DATED         : December 24, 2002
INVENTOR(S)   : Glombik et al.

It is certified that error appears in the above-identified patent and that said Letters Patent is hereby corrected as shown below:

Column 51,
Line 31, "$SO_2$-$(_1$-$C_6)$-alkyl" should read -- $SO_2$-$(C_1$-$C_6)$-alkyl --.
Line 43, "is shown" should read -- L is shown --.

Column 52,
Lines 11 and 57, "$SO_2$-$(H_2)_n$-phenyl" should read -- $SO_2$-$(CH_2)_n$-phenyl --.
Line 22, "is shown" should read -- L is shown --.
Lines 56-57, "$SO_2$-$(_1$-$C_6)$-alkyl" should read -- $SO_2$-$(C_1$-$C_6)$-alkyl --.

Column 53,
Lines 1 and 49, "is shown" should read -- L is shown --.
Line 38, "$SO_2$-$(H_2)_n$-phenyl" should read -- $SO_2$-$(CH_2)_n$-phenyl --.

Column 54,
Line 14, "claimed claim" should read -- claimed in claim --.

Signed and Sealed this

Eighteenth Day of March, 2003

JAMES E. ROGAN
*Director of the United States Patent and Trademark Office*